(12) United States Patent
Burke et al.

(10) Patent No.: US 12,730,100 B2
(45) Date of Patent: Sep. 8, 2026

(54) MEASUREMENT AND CONTROL OF ENTRAINED AIR AND FOAM IN METALWORKING FLUIDS

(71) Applicant: QUAKER CHEMICAL CORPORATION, Wilmington, DE (US)

(72) Inventors: John Burke, Wilmington, DE (US); Alan Cross, Wilmington, DE (US)

(73) Assignee: QUAKER CHEMICAL CORPORATION, Wilmington, DE (US)

( * ) Notice: Subject to any disclaimer, the term of this patent is extended or adjusted under 35 U.S.C. 154(b) by 412 days.

(21) Appl. No.: 18/327,970

(22) Filed: Jun. 2, 2023

(65) Prior Publication Data

US 2023/0358722 A1 Nov. 9, 2023

Related U.S. Application Data

(63) Continuation of application No. 17/929,019, filed as application No. PCT/US2021/017424 on Feb. 10, 2021.

(Continued)

(51) Int. Cl.
*G01N 33/28* (2006.01)
*G01N 7/14* (2006.01)

(52) U.S. Cl.
CPC .......... *G01N 33/2841* (2013.01); *G01N 7/14* (2013.01); *G01N 33/2894* (2013.01)

(58) Field of Classification Search
None
See application file for complete search history.

(56) References Cited

U.S. PATENT DOCUMENTS 3,151,061 A * 9/1964 Orr ........................ B01J 19/002 208/341
4,003,724 A * 1/1977 Payne .................. B01J 19/0006 137/170.2

(Continued)

FOREIGN PATENT DOCUMENTS

CA 2274707 A1 * 7/1998 ........ C10M 171/004
CN 102087259 B * 3/2014

(Continued)

OTHER PUBLICATIONS

International Search Report and Written Opinion for International Patent Application No. PCT/US2021/017424, 12 pages, mailed Jun. 23, 2021.

(Continued)

*Primary Examiner* — Daniel S Larkin
(74) *Attorney, Agent, or Firm* — Morgan, Lewis & Bockius LLP

(57) ABSTRACT

Systems and methods for measuring air withing a fluid and for mitigating damage to a metalworking tool are disclosed. A system for measuring air within a fluid includes a fluid path having a first end and a second end; a first valve having an open position and a closed position, wherein fluid can pass through the first valve in the open position and fluid is prevented from passing through the first valve in the closed position; a first sensor located between the first valve and the second end; and a second sensor located between the first sensor and the second end, wherein the second end is higher than the first end.

10 Claims, 20 Drawing Sheets

Related U.S. Application Data

(60) Provisional application No. 62/975,097, filed on Feb. 11, 2020.

(56) References Cited

U.S. PATENT DOCUMENTS

| | | | | | |
|---|---|---|---|---|---|
| 4,858,460 | A | | 8/1989 | Schohl et al. | |
| 4,938,072 | A | | 7/1990 | Brown et al. | |
| 5,062,292 | A | * | 11/1991 | Kanba | G01N 33/2841 73/19.1 |
| 5,127,962 | A | * | 7/1992 | Inoue | G01N 25/14 134/22.12 |
| 5,295,083 | A | | 3/1994 | Yano et al. | |
| 5,361,624 | A | * | 11/1994 | Lambert | G01N 27/49 73/19.1 |
| 5,375,459 | A | * | 12/1994 | Gerke | G01N 13/00 73/60.11 |
| 5,597,950 | A | * | 1/1997 | Mullen | G01N 27/06 73/866 |
| 5,965,805 | A | * | 10/1999 | Watts | G01N 9/04 73/19.11 |
| 2003/0172716 | A1 | * | 9/2003 | Braesel | G01N 33/2841 73/19.1 |
| 2005/0109078 | A1 | | 5/2005 | Chen et al. | |
| 2013/0118234 | A1 | | 5/2013 | Jeon | |
| 2014/0090421 | A1 | | 4/2014 | Shock et al. | |
| 2017/0212093 | A1 | | 7/2017 | Virtanen et al. | |

FOREIGN PATENT DOCUMENTS

| | | | | | |
|---|---|---|---|---|---|
| DE | 29606210 | U1 | | 6/1996 | |
| EP | 380759 | A | * | 8/1990 | G01N 9/04 |
| EP | 0380759 | B1 | | 3/1994 | |
| JP | H0353159 | A | * | 3/1991 | |
| KR | 20190079051 | A | * | 7/2019 | H01F 27/402 |

OTHER PUBLICATIONS

International Preliminary Report on Patentability for related International Patent Application No. PCT/US2021/017424, dated Jun. 23, 2021, 8 pages.

Extended Search Report issued in corresponding European Patent Application No. 21753697.8, dated Apr. 24, 2024, 16 pages.

Office Action issued in corresponding Canadian Patent Application No. 3,164,377, dated Jul. 25, 2024, 3 pages.

Preliminary Report on Patentability issued in corresponding International Patent Application No. PCT/US2021/017424, dated Jun. 23, 2021, 8 pages.

* cited by examiner

Metal Adhesion (BUE) on Drill Cutting Edge

Metal Adhesion (BUE) on Drill Cutting Edge

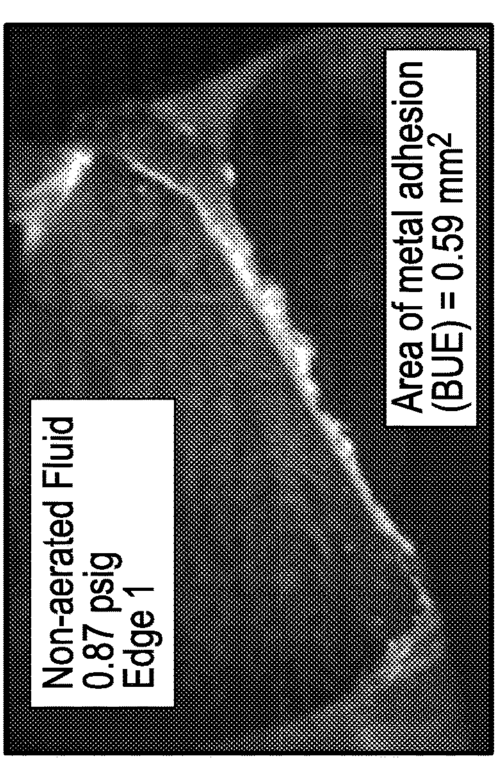
FIG. 10A
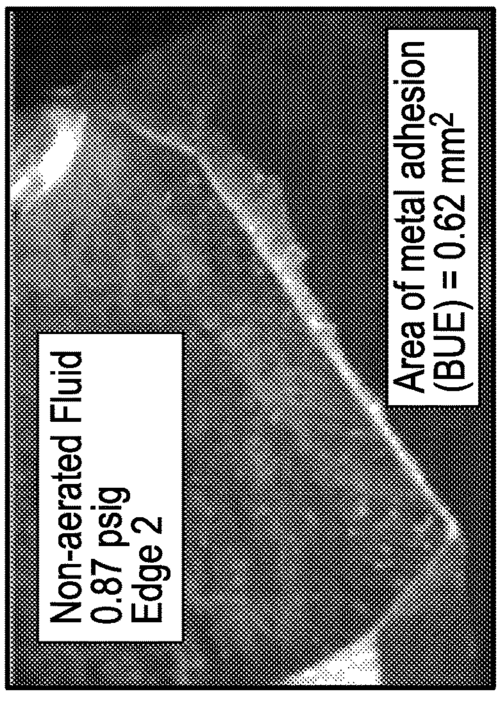
FIG. 10B
Aerated Fluid
0.79 psig
Edge 1
Area of metal adhesion
(BUE) = 1.10 mm$^2$
FIG. 10C
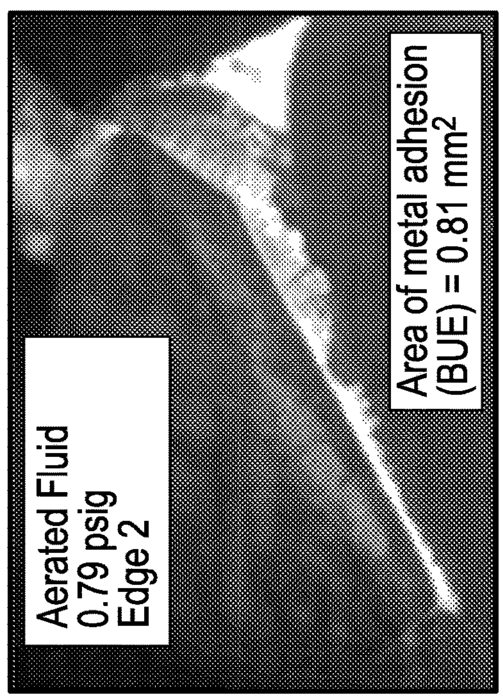
FIG. 10D Microtap Tests on 5.0% Hocut 795-MPC and 1018 steel bars with and without entrained air Average Torque, Ncm 290.0
285.0
280.0
275.0
270.0
265.0
260.0

273.7
281.6
276.2

Initial, no air
With entrained air
Final, no air

FIG. 19

MEASUREMENT AND CONTROL OF ENTRAINED AIR AND FOAM IN METALWORKING FLUIDS

CROSS-REFERENCE TO RELATED APPLICATION

This application is a continuation of U.S. patent application Ser. No. 17/929,019, filed Aug. 10, 2022, which is a U.S. National Stage Entry of International Patent Application Serial No. PCT/US2021/017424, filed on Feb. 10, 2021, which in turn claims priority to U.S. Provisional Patent Application No. 62/975,097 filed on Feb. 11, 2020, which is hereby incorporated by reference in its entirety.

BACKGROUND OF THE INVENTION

The present invention generally relates to methods and systems for measurement of air within a fluid.

Metalworking fluids (MWF) are used in various processing of metals. For example, metalworking fluids are used in metal removal, treating, protecting and forming, as well as metal cleaning. In such processes, fluids are sprayed onto metal parts, or metal parts are dipped into fluids. The used fluids are recirculated back to a reservoir and recycled using methods, such as filtering or relying on gravity, to separate out particulate material from the fluids. After recycling, the fluid is recirculated to the processing step.

Many such metalworking processes are now performed under high pressure and/or high velocity. High pressure and/or high velocity can result in air and/or foam build up in the fluid. An efficient method of measuring the amount of air and/or foam in the fluid is needed.

BRIEF SUMMARY OF THE INVENTION

In some embodiments, there is a system for measuring air within a fluid. The system may include a fluid path having a first end and a second end; a first valve having an open position and a closed position, wherein fluid can pass through the first valve in the open position and fluid is prevented from passing through the first valve in the closed position; a first sensor located between the first valve and the second end; and a second sensor located between the first sensor and the second end, wherein the second end is higher than the first end.

The system may also include a fluid outlet located between the second sensor and the second end. The system may also include a second valve and a fluid drain, wherein the second valve has an open position and a closed position, wherein fluid can pass through the second valve in the open position and is prevented from passing through the second valve in the closed position, and wherein the second valve is located below the first sensor.

In some embodiments, the first sensor is a pressure transducer.

The system may also include a computerized device programmed to calculate the amount of air entrained within the fluid based on measurements of the first sensor. The system may also include a computerized device programmed to calculate the amount of foam within a fluid based on measurements of the second sensor.

In some embodiments, a system for measuring air within a fluid includes a fluid path; a first valve having an open position and a closed position, wherein fluid can pass through the first valve in the open position and fluid is prevented from passing through the first valve in the closed position; a second valve having an open position and a closed position, wherein fluid can pass through the second valve in the open position and fluid is prevented from passing through the second valve in the closed position; and a first sensor located between the first valve and the second valve, wherein the second valve is located higher than the first valve.

The system may also include a second sensor located between the first sensor and the second valve, wherein the second sensor is located a fixed distance from the first sensor. The system may also include a fluid outlet located between the second sensor and the second valve. The system may also include a third valve and a fluid drain, wherein the third valve has an open position and a closed position, wherein fluid can pass through the third valve in the open position and is prevented from passing through the third valve in the closed position, and wherein the third valve is located between the first sensor and the fluid drain.

In some embodiments, the first sensor is a pressure transducer. In some embodiments the second sensor is a pressure transducer.

In some embodiments, a system for measuring air within a fluid includes a fluid path having a first inlet, a first outlet, a second inlet, and a second outlet; a first, second, third, and fourth valves each independently having an open position and a closed position, wherein the fluid can pass through each valve in the open position and the fluid is prevented from passing through each valve in the closed position; and a first sensor, wherein the first outlet is higher than the first inlet, wherein the second outlet is higher than the second inlet, wherein the first valve is located between the first inlet and the first outlet, wherein the second valve is located between the second inlet and the second outlet, wherein the third valve is located between the first outlet and the first sensor, and wherein the fourth valve is located between the second outlet and the first sensor. The first sensor may be a pressure transducer.

The system may also include a computerized device programmed to calculate the amount of air entrained within the fluid based on measurements of the first and second sensors and the fixed distance between the first and second sensors. The system may also include a computerized device programmed to calculate the amount of foam within a fluid based on measurements of the first and second sensors and the fixed distance between the first and second sensors.

In some embodiments, a method of measuring air within a fluid includes passing a fluid substantially vertically through a fluid conduit; stopping the flow of the fluid through the fluid conduit at a first time point; measuring the pressure of the fluid at a first position along the fluid conduit at the first time point to acquire a first pressure measurement and at a subsequent time point to acquire a subsequent pressure measurement; calculating the percent change in fluid pressure measurement between the first time point and the subsequent time point; and correlating the percent change in fluid pressure measurement to change in mass percent of air within the fluid.

In some embodiments, a method of measuring air within a fluid includes passing a fluid substantially vertically through a fluid conduit; stopping the flow of the fluid through the fluid conduit at a first time point; measuring the pressure of the fluid at a first position along the fluid conduit at the first time point, a penultimate time point, and a final time point to acquire a first pressure measurement, a penultimate pressure measurement, and a final pressure measurement; calculating the density of the fluid at the first time point, the penultimate time point, and the final time point from the pressure of the fluid at the first time point, the penultimate time point, and the final time point, respectively; calculating the change in density of the fluid as a function of time; and calculating the amount of air within the fluid at the first time point based on the change in density of the fluid as a function of time.

The method of measuring air within a fluid may also include measuring the pressure of the fluid at the first position along the fluid conduit at one or more subsequent time points after the first time point and before the penultimate time point to acquire one or more subsequent pressure measurements; and calculating the density of the fluid at the subsequent time points based on the subsequent pressure measurements. In some embodiments, the final pressure measurement is substantially the same as the penultimate pressure measurement. In some embodiments, the final density of the fluid is substantially the same as the density of the fluid that is substantially free of entrained air.

In some embodiments, a method of measuring the amount of foam within a fluid includes passing a fluid substantially vertically through a fluid conduit; stopping the flow of the fluid through the fluid conduit at a first time point; measuring the pressure of the fluid at a first position along the fluid conduit at the first time point, a penultimate time point, and a final time point to acquire a first pressure measurement, a penultimate pressure measurement, and a final pressure measurement; calculating the density of the fluid at the first time point, the penultimate time point, and the final time point from the pressure of the fluid at the first time point, the penultimate time point, and the final time point, respectively; calculating the change in density of the fluid as a function of time; and calculating the amount of air within the fluid at the first time point based on the change in density of the fluid as a function of time. The method may also include measuring the pressure of the fluid at the first position along the fluid conduit at one or more subsequent time points after the first time point and before the penultimate time point to acquire one or more subsequent pressure measurements; and calculating the density of the fluid at the subsequent time points based on the subsequent pressure measurements. In some embodiments the final pressure measurement is substantially the same as the penultimate pressure measurement.

In some embodiments, a method for preventing or minimizing damage to a metalworking tool, the method includes monitoring of the amount of air entrained within a metalworking fluid, mitigating the amount of air entrained within the metalworking fluid when the amount of air detected is about 5% by mass of the fluid or greater.

In some embodiments, a method for preventing or minimizing damage to a metalworking tool, the method includes detecting a baseline pressure of a metalworking fluid; monitoring the change in the pressure of the metalworking fluid over time; and mitigating an amount of air entrained within the metalworking fluid when the pressure of the metalworking fluid has decreased by about 5% or more. In some embodiments, mitigating comprises reducing the amount of air entrained within the metalworking fluid to less than about 5% by mass of the fluid. In some embodiments, mitigating comprises reducing the amount of air entrained within the metalworking fluid to about the baseline amount of air entrained within the metalworking fluid or less. In some embodiments, mitigating comprises replacing the metalworking fluid with a second metalworking fluid having a pressure that is about 103% of the baseline pressure of the metalworking fluid or less. In some embodiments, mitigating comprises adding an additive to the metalworking fluid. Suitable additives include defoamers, such as a defoamer comprising a one or more of a polyacrylate, a siloxane, a silicone, and an oil. In some embodiments, damage is metal adhesion to the metalworking tool.

BRIEF DESCRIPTION OF THE SEVERAL VIEWS OF THE DRAWINGS

The following detailed description of embodiments of the system for measuring air in a fluid, will be better understood when read in conjunction with the appended drawings of exemplary embodiments. It should be understood, however, that the invention is not limited to the precise arrangements and instrumentalities shown.

In the drawings:

FIGS. 10A, 10B, 10C, and 10D provide images of metal adhesion on an edge of a drilling tool used with fluid with minimal entrained air or used with fluid with entrained air. FIG. 10A provides an image of metal adhesion on a first edge of a drilling tool used with fluid with minimal entrained air. FIG. 10B provides an image of metal adhesion on a second edge of a drilling tool used with fluid with minimal entrained air. FIG. 10C provides an image of metal adhesion on a first edge of a drilling tool used with fluid with entrained air. FIG. 10D provides an image of metal adhesion on a second edge of a drilling tool used with fluid with entrained air.

FIG. 12A illustrates a reamer surface after use with a fluid with minimal entrained air. FIG. 12B illustrates a reamer surface after use with a fluid with entrained air.

FIG. 13A illustrates a spring-loaded three stone honing tool, a drilled and pre-honed bore, and application of a metal-working fluid. FIG. 13B illustrates another view of the spring-loaded three stone honing tool, a drilled and pre-honed bore, and application of a metal-working fluid of FIG. 13A. FIG. 13C illustrates a close-up picture of a stone used with the honing tool shown in FIGS. 13A and 13B.

FIG. 18A provides pictures of a honing stone used with a Quakercool 8013 fluid with minimal entrained air. FIG. 18B provides pictures of a honing stone used with a Quakercool 8013 fluid with entrained air.

FIG. 19 provides a graphic of the torque measurements obtained with the two fluids during the tapping of Steel 1018.

DETAILED DESCRIPTION OF THE INVENTION

Figure 1:
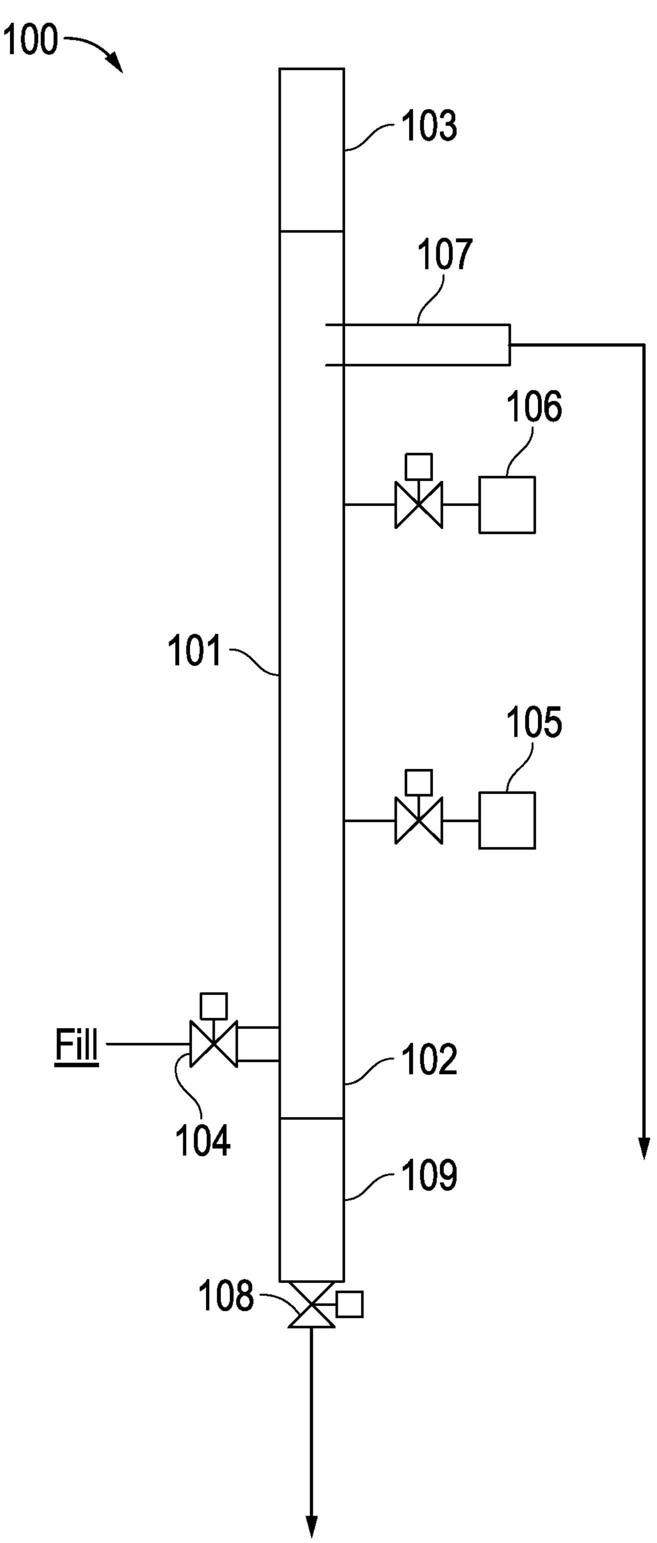
FIG. 1 illustrates aspects of a system for measuring air in a fluid, in accordance with an exemplary embodiment of the present invention.

Certain embodiments of the present invention include systems for measuring the amount of air within a fluid. Systems of the invention may be used for measuring the amount of foam in a fluid, or the amount of air entrained within the fluid. For purposes of this description, fluid refers to any liquid, for example a metalworking fluid (MWF) and air refers to any gas, for example the mixture of gases surrounding the Earth.

Air in machinery fluids, such as metalworking fluids, can be problematic. Fluids being used as a lubricant can have their lubricant quality decreased as air is not a lubricant. Fluid pumps are generally not designed to pump air and the presence of air in a fluid can cause damage to the internal mechanisms of the pump. The presence of air in a heat transfer fluid can result in heat not being properly transferred. In each of these examples, the presence of air in a fluid, whether in the form of entrained air within the fluid or as foam, can result in damage to parts and tools. Embodiments of systems and methods of the present invention allow for the build-up of air in a fluid to be recognized and mitigated before damage to equipment and tools is incurred, saving time and money.

Systems and methods according to the invention are useful for preventing damage to tools and equipment associated with a wide variety of machining operations, including but not limited to drilling, boring, reaming, tapping, thread rolling, thread chasing, hobbing, milling, turning, sawing, planning, scraping, shearing, shaving, broaching, cutting, polishing, burnishing. Systems and methods according to the invention are useful for preventing damage to tools and equipment associated with a wide variety of impact deformation processes, including but not limited to stamping, cold forging, and hot forging. Systems and methods according to the invention are useful for preventing damage to tools and equipment associated with a wide variety pressure deformation processes including, but not limited to hydroforming and sintering.

Systems and methods according to some embodiments of the invention determine the amount of entrained air in a fluid and the amount of time required for all entrained air to leave the fluid. In some embodiments, the entrained air and foam can be controlled by dispensing a foam/entrained air control agent into the system in which the fluid is used. Some embodiments of the invention work by measuring the density of an in-use fluid, letting the fluid sit undisturbed while continuously measuring the density of the fluid as the air is released, and determining the amount of entrained air in the fluid through the gathered density data. In some embodiments, a defoamer or air-release fluid is then dispensed into the fluid. This can be done in a flowing fluid environment or a stagnant fluid environment, with one or two pressure transducers for the density measurement.

Referring to the drawings in detail, wherein like reference numerals indicate like elements throughout, there is shown in FIGS. 1-4 systems for measuring air in a fluid in accordance with an exemplary embodiment of the present invention. It should be understood that the present subject matter can, however, be embodied in different forms and should not be construed as limited to the illustrated embodiments set forth herein. It should also be apparent that individual elements identified herein as belonging to a particular embodiment may be included in other embodiments of the invention.

FIG. 1 depicts a system (100) for measuring air in a fluid according to an embodiment of the invention. Fluid path (101) comprises a first end (102) and a second end (103). Fluid path (101) may be oriented with the second end (103) higher than first end (102) such that any gas or air within the liquid fluid system rises towards the second end when flow of the fluid pauses. In some embodiments the second end (103) may be open to the atmosphere, while in other embodiments, the second end (103) may connect to additional fluid circuitry. System 100 may include a first valve (104) having an open position and a closed position, wherein fluid can pass through the first valve (104) in the open position and fluid is prevented from passing through the first valve (104) in the closed position. System (100) may include a first sensor (105) located between the first valve (104) and the second end (103). In some embodiments, system (100) may include a second sensor (106) located between the first sensor (105) and the second end (103). Sensors (105, 106) are useful for measuring the pressure of the fluid in the system and in some embodiments may be pressure transducers. Sensors (105,106) may be other devices for measuring the pressure or density of a fluid in certain embodiments. System (100) may further include a fluid outlet (107) located between the second sensor (106) and the second end (103). The fluid outlet (107) may be used as a release for gas from the fluid in the system, or as an outlet for overflow fluid, or both.

As shown, system (100) of FIG. 1 may further include a second valve (108) having an open position and a closed position, such that fluid can pass through the second valve (108) in the open position and is prevented from passing through the second valve (108) in the closed position. System (100) may further comprise a fluid drain (109) for draining the fluid path (101) of fluid. Second valve (108) may be located in or adjacent to fluid drain (109) so as to control the release of fluid through fluid drain (109). Second valve (108) may be located below the first sensor (105).

In some embodiments, system (100) may further include a computerized device programmed to calculate the amount of air entrained within the fluid based on measurements of the first sensor (105) and/or second sensor (106). In some embodiments, system (100) may include a computerized device programmed to calculate the amount of foam within a fluid based on measurements of the first sensor (105) and/or second sensor (106).

Figure 2:
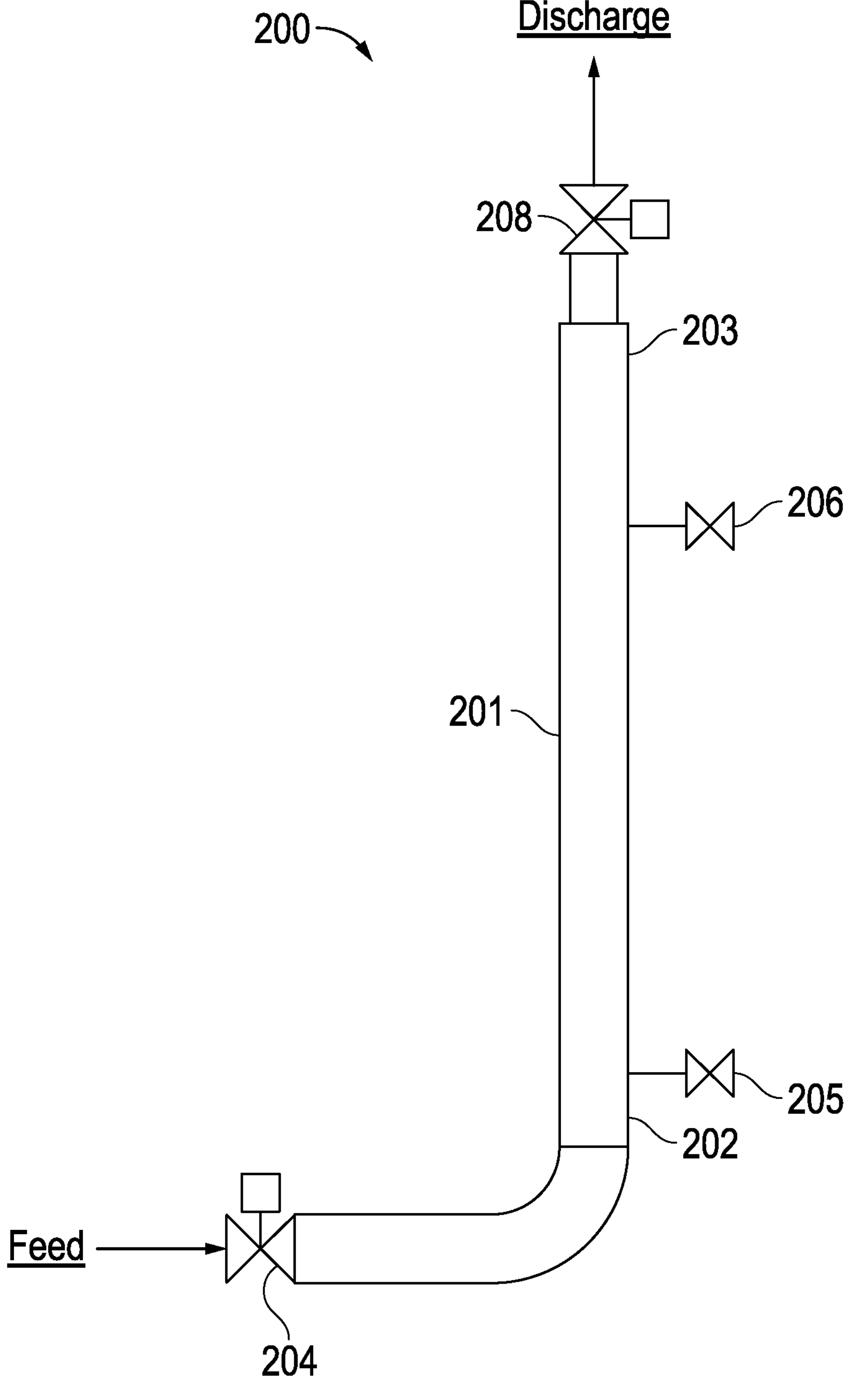
FIG. 2 illustrates aspects of a system for measuring air in a fluid, in accordance with an exemplary embodiment of the present invention.

FIG. 2 shows a system (200) for measuring air in a fluid according to an embodiment of the invention. System (200) includes a fluid path (201). Fluid path (201) may be a part of a greater fluid circuit. Fluid path (201) may comprise a first end (202) and a second end (203). Fluid path (201) may be oriented with the second end (203) higher than first end (202) such that any gas or air within the liquid fluid system rises towards the second end (203) when flow of the fluid pauses. System 200 may include a first valve (204) having an open position and a closed position, wherein fluid can pass through the first valve (204) in the open position and fluid is prevented from passing through the first valve (204) in the closed position. System 200 may include a second valve (208) having an open position and a closed position, wherein fluid can pass through the first valve (208) in the open position and fluid is prevented from passing through the first valve (208) in the closed position. Valves (204, 208) of system (200) may be arranged such that the fluid path is part of a greater fluid circuit and the amount of air in the fluid can be measured by controlling valves (204, 208) without rerouting the flow of the fluid. As shown in FIG. 2, first valve 204 may be used to allow fluid into the fluid path and to close the first end of the fluid path in order to measure the density and/or pressure of the fluid in the system. Similarly, as shown in FIG. 2, second valve (208) may be used to contain fluid within the fluid path or to provide an outlet from the fluid path.

System (200) may include a first sensor (205) located between the first valve (204) and the second valve (208). In some embodiments, system (200) may include a second sensor (206) located between the first sensor (205) and the second valve (208). Sensors (205, 206) are useful for measuring the pressure of the fluid in the system and in some embodiments may be pressure transducers. Sensors (205, 206) may be other devices for measuring the pressure or density of a fluid in certain embodiments. System (200) may further include a fluid outlet (not depicted), for example, located between the second sensor (206) and the second valve (208). The fluid outlet may be used as a release for gas from the fluid in the system, or as an outlet for overflow fluid, or both.

In some embodiments, system (200) may further include a computerized device programmed to calculate the amount of air entrained within the fluid based on measurements of the first sensor (205) and/or second sensor (206). In some embodiments, system (200) may include a computerized device programmed to calculate the amount of foam within a fluid based on measurements of the first sensor (205) and/or second sensor (206).

Figure 3:
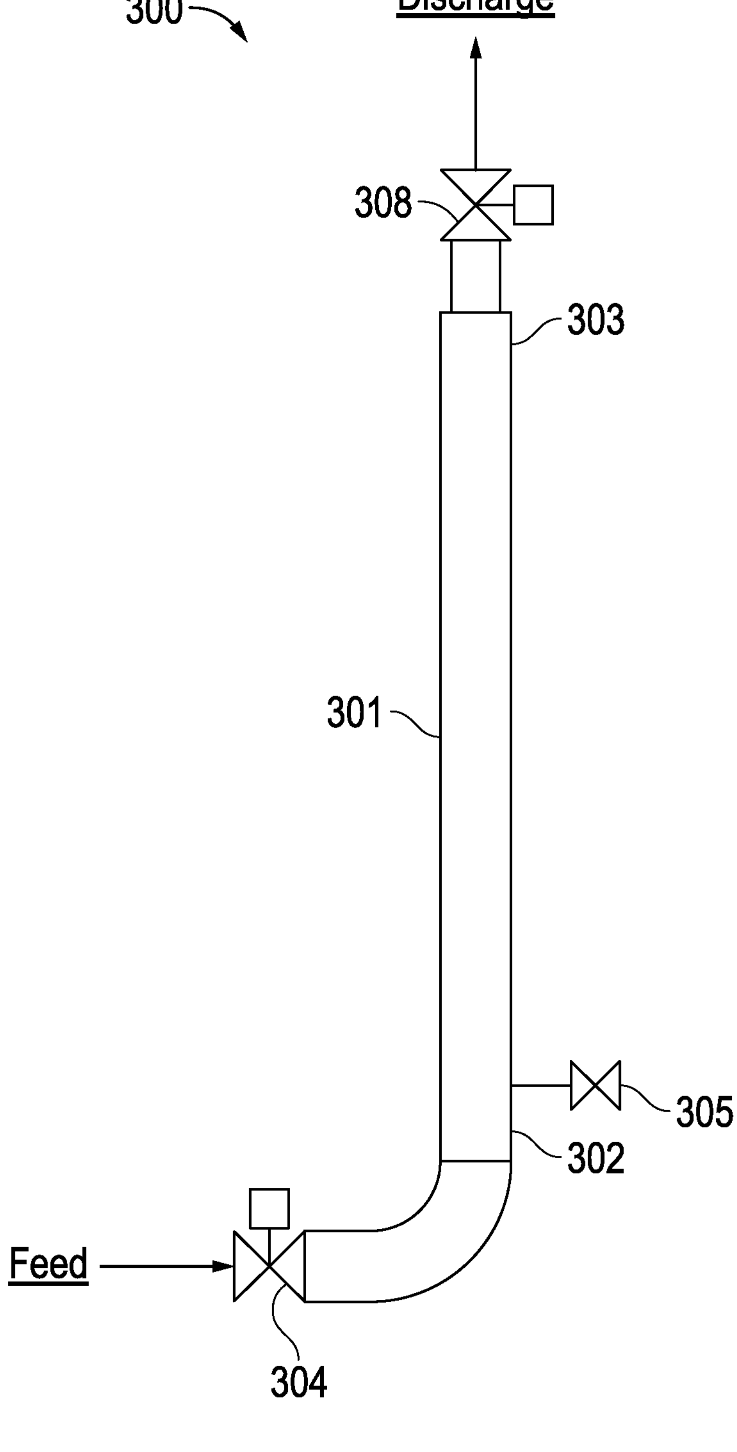
FIG. 3 illustrates aspects of a system for measuring air in a fluid, in accordance with an exemplary embodiment of the present invention.

FIG. 3 shows a system (300) for measuring air in a fluid according to an embodiment of the invention. System (300) includes a fluid path (301). Fluid path (301) may comprise a first end (302) and a second end (303). Fluid path (301) may be a part of a greater fluid circuit. Fluid path (301) may be oriented with the second end (303) higher than first end (302) such that any gas or air within the liquid fluid system rises towards the second end (303) when flow of the fluid pauses. System 300 may include a first valve (304) having an open position and a closed position, wherein fluid can pass through the first valve (304) in the open position and fluid is prevented from passing through the first valve (304) in the closed position. System 300 may include a second valve (308) having an open position and a closed position, wherein fluid can pass through the first valve (308) in the open position and fluid is prevented from passing through the first valve (308) in the closed position. Valves (304, 308) of system (300) may be arranged such that the fluid path is part of a greater fluid circuit and the amount of air in the fluid can be measured by controlling valves (308, 304). As shown in FIG. 3, first valve 304 may be used to allow fluid into the fluid path and to close the first end of the fluid path in order to measure the density and/or pressure of the fluid in the system. Similarly, as shown in FIG. 3, second valve (308) may be used to contain fluid within the fluid path or to provide an outlet from the fluid path.

System (300) may include a first sensor (305) located between the first valve (304) and the second valve (308). Sensor (305) may be useful for measuring the pressure or density of the fluid in the system and in some embodiments may be a pressure transducer.

In some embodiments, system (300) may further include a computerized device (not depicted) programmed to calculate the amount of air entrained within the fluid based on measurements of the first sensor (305). In some embodiments, system (300) may include a computerized device programmed to calculate the amount of foam within a fluid based on measurements of the first sensor (305).

Figure 4:
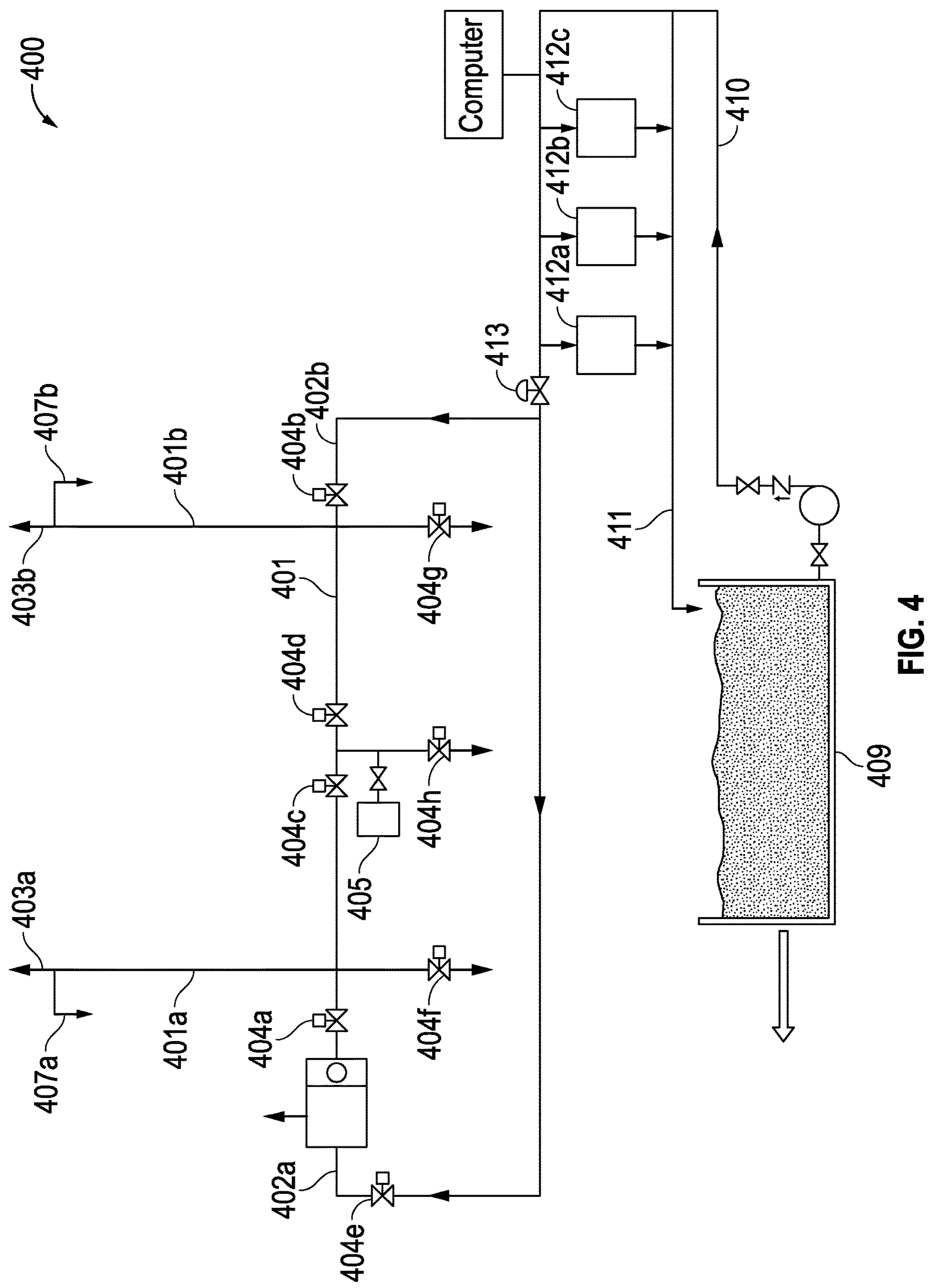
FIG. 4 illustrates aspects of a system for measuring air in a fluid, in accordance with an exemplary embodiment of the present invention.

FIG. 4 shows a system (400) for measuring air in a fluid according to an embodiment of the invention. System (400) comprises fluid path (401), which includes a reference path (401*a*) and a measurement path (401*b*). It is possible that the density of a fluid changes over time, independent of the amount of air in the fluid, complicating the calculation of the amount of air entrained within the fluid based on change in density. In some embodiments, providing a reference path (401*a*) and a measurement path (401*b*) allows for the density of the fluid to be monitored independently of the measurement of the amount of air entrapped in the same fluid. Reference path (401*a*) may have a first end (402*a*) and a second end (403*a*). Measurement path (401*b*) may have a first end (402*b*) and a second end (403*b*). The reference path (401*a*) and the measurement path (401*b*) may each independently be oriented with the second end (403*a*, 403*b*) higher than first end (402*a*, 402*b*) such that any gas or air within the liquid fluid system rises towards the second end (403*a*, 403*b*) when flow of the fluid is paused. Second end (403*a*, 403*b*) may be open to the atmosphere or may fluidly connect to a fluid reservoir (409). In some embodiments where the second end (403*a*, 403*b*) vents to the atmosphere one, or more fluid outlets (407*a*, 407*b*) may be included to fluidly connect reference path (401*a*) and/or measurement path (401*b*) with a fluid reservoir (409).

As shown in FIG. 4, the flow of the fluid through the fluid path (401) can be controlled by a plurality of valves (404*a*, 404*b*, 404*c*, 404*d*, 404*e*, 404*f*, 404*g*, 404*h*). System 400 may include a plurality of valves (404) each having an open position and a closed position, wherein fluid can pass through the valve (404) in the open position and fluid is prevented from passing through the valve (404) in the closed position. System (400) may include a first sensor (405). Sensor (405) may be useful for measuring the pressure or density of the fluid in the system and in some embodiments may be a pressure transducer.

Valve (404*a*) allows or prevents fluid from entering the reference path (401*a*). Similarly, valve (404*b*) allows or prevents fluid from entering measurement path (401*b*).

Valve (404*f*) retains fluid in reference path (401*a*) when closed and allows fluid to drain or return to the fluid reservoir (409) when open. Similarly, valve (404*g*) retains fluid in measurement path (401*b*) when closed and allows fluid to drain or return to the fluid reservoir (409) when open. Valve (404*c*) allows fluid in reference path (401*a*) to reach sensor (405). Similarly, valve (404*d*) allows fluid in measurement path (401*b*) to reach sensor (405). Sensor 405 may be useful for measuring the pressure or density of the fluid in the system and in some embodiments may be a pressure transducer. Valve (404*h*) retains fluid so a measurement can be obtained with sensor (405) when closed, and allows fluid to drain or return to the fluid reservoir (409) when open. In some embodiments, additional valves may be included, for example valve (404*e*). In some embodiments, a specialty valve may be included, for example as shown in FIG. 4, pressure reducing valve (413).

System (400) may include one or more machine tools (412*a*, 412*b*, 412*c*). System (400) may include a clean fluid path (410) fluidly connecting the fluid reservoir (409) with one or more machine tools (412*a*, 412*b*, 412*c*) and/or reference path (401*a*) and/or measurement path (401*b*). The direction of the fluid from fluid reservoir (409) to machine tools (412) or reference path may be controlled by one or more valves. System (400) may include a drain line (411) for returning fluid from reference path (401*a*), measurement path (401*b*), or otherwise from fluid path (401) to the fluid reservoir (409). In some embodiments, drain line (411) may fluidly connect machine tools (412) to fluid reservoir (409) for returning used fluid from such tools to the reservoir.

In some embodiments, system (400) may further include a computerized device (not depicted) programmed to calculate the amount of air entrained within the fluid based on measurements of the sensor (405). In some embodiments, system (400) may include a computerized device programmed to calculate the amount of foam within a fluid based on measurements of the sensor (405).

In one embodiment, the system includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

Methods for measuring air or foam within a fluid are disclosed. In some embodiments, a method of measuring air or foam within a fluid includes passing a fluid through a fluid path, stopping the flow of the fluid through the fluid path at a first time point; and measuring the pressure of the fluid at a first position along the fluid path at the first time point. In some embodiments, the method further includes after measuring the pressure of the fluid at the first time point, passing the fluid through the fluid path, stopping the flow of the fluid through the fluid path at a second time point, and measuring the pressure of the fluid at the first position at the second time point. In some embodiments, the pressure measurement can be correlated to the mass of entrained air in the fluid. For example, in some embodiments, an initial or baseline pressure measurement taken before shearing or other disturbance of the fluid can be correlated to 0% by mass entrained air within the fluid. A reduction in the pressure of the fluid measured at a subsequent time point can be attributed to an increase in air within the fluid, such that the percent reduction in the pressure correlates to the increase in mass percent of air within the fluid.

In some embodiments, a method of measuring air or foam within a fluid includes passing a fluid through a fluid path, stopping the flow of the fluid through the fluid path at a first time point; measuring the pressure of the fluid at a first position along the fluid path at the first time point, a penultimate time point, and a final time point to acquire a first pressure measurement, a penultimate pressure measurement, and a final pressure measurement, respectively. A pressure transducer can be used for measuring the pressure of the fluid. The fluid path may be oriented substantially vertically to allow entrained air to escape the fluid over time.

The method may further include calculating the density of the fluid at the first time point, the penultimate time point, and the final time point from the pressure of the fluid at the first time point, the penultimate time point, and the final time point, respectively. The method may further include calculating the change in density of the fluid as a function of time. In some embodiments, the density can be measured directly instead of measuring the pressure and then calculating the density.

In some embodiments, the pressure of the fluid at the first position along the fluid conduit is measured at one or more subsequent time points after the first time point and before the penultimate time point to acquire one or more subsequent pressure measurements. The density of the fluid at the subsequent time points may be calculated based on the subsequent pressure measurements. It may be determined that sufficient measurements have been taken when successive pressure measurements are substantially the same. For example, the final pressure measurement may be substantially the same as the penultimate pressure measurement.

In some embodiments, a method includes calculating the amount of air within the fluid at the first time point based on the change in density of the fluid as a function of time. In some embodiments, a method includes calculating the amount of air within the fluid at the first time point based on the change in pressure of the fluid as a function of time. In some embodiments, the final density of the fluid is substantially the same as the density of the fluid that is substantially free of entrained air.

In some embodiments, a method includes calculating the amount of foam within the fluid at the first time point based on the change in density of the fluid as a function of time. In some embodiments, a method includes calculating the amount of foam within the fluid at the first time point based on the change in pressure of the fluid as a function of time.

In some embodiments, the amount of foam present is first determined, then after the foam has completely broken down, the amount of entrained air can be determined. The amount of foam and the amount of entrained air can be determined through the same process of taking a series of pressure measurements and calculating the change in the density of the fluid over time. For example, by waiting for a penultimate time the foam can be present first, then after that set time the entrained air will be a subsequent measurement. The time difference will first be a foam measurement and the second will be an entrained air measurement, with the times being set based upon the fluid and field conditions.

Figure 5:
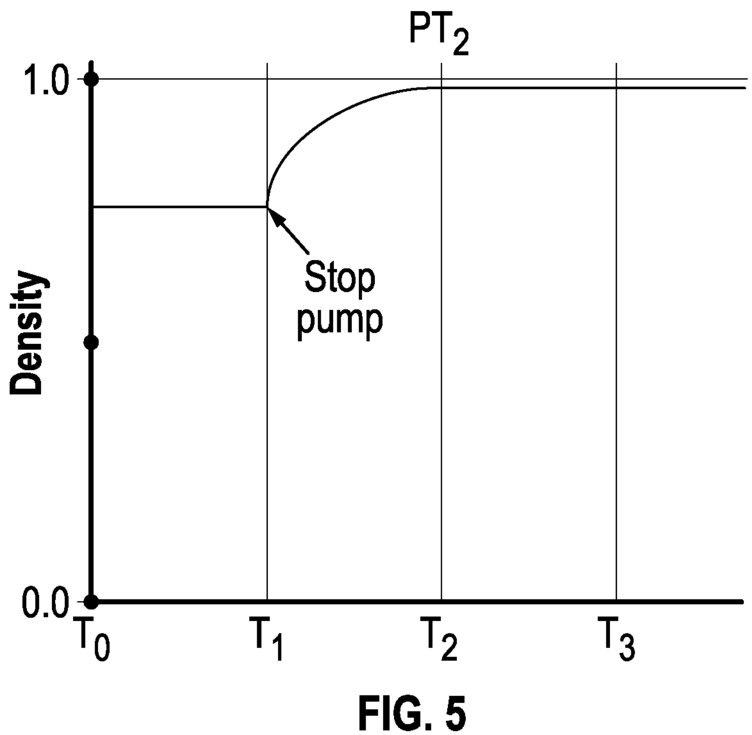
FIG. 5 illustrates the change in density of a fluid over time.

FIG. 5 shows the change in density of a fluid measured in a system according to an embodiment of the invention over time. At an initial time point, $T_0$, the fluid is circulating through the system. At time point $T_1$, the fluid is stopped from circulating, for example, by stopping a pump circulating fluid from a fluid reservoir, or by closing a valve, preventing the continued flow of the fluid. A sensor may be used to measure the pressure of the fluid, from which the density of the fluid can be calculated. In other embodiments, a sensor may be used to measure the density of the fluid directly. The density of the fluid is determined at various time points ($T_0$, $T_1$, $T_2$, $T_3$) after the flow of the fluid is stopped. As the air escapes the fluid, such as into the atmosphere through a vent, the density of the fluid gradually returns to the density of the fluid with no air and the density measurement will stabilize. The amount of air entrained within the fluid can be calculated based on the slope of the curve of the density measurements over time.

Figure 6:
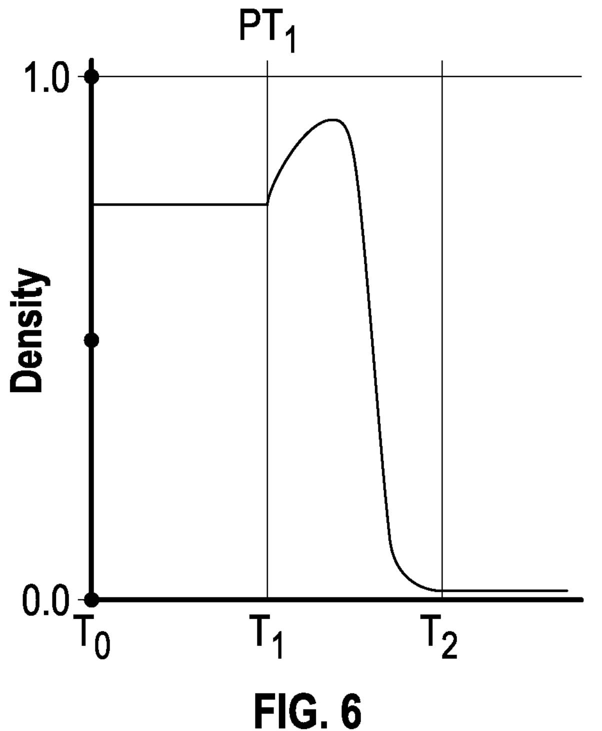
FIG. 6 illustrates the change in foam pressure over time.

FIG. 6 shows the change in foam pressure measured in a system according to an embodiment of the invention over time. At an initial time point, $T_0$, the fluid is circulating through the system. At time point $T_1$, the fluid is stopped from circulating, for example, by stopping a pump circulating fluid from a fluid reservoir, or by closing a valve, preventing the continued flow of the fluid. A sensor may be used to measure the pressure of the foam. Initially the foam will increase until the foam begins to break down, at which point the fluid pressure will continue to decrease until the foam has dissipated. The amount of time needed for the foam to break down, or for the foam pressure to approach zero (around $T_2$), can be used to calculate the amount of foam within the fluid.

In some embodiments, a method preventing or minimizing damage to a metalworking tool, comprises monitoring of the amount of air entrained within a metalworking fluid and mitigating the amount of air entrained within the metalworking fluid when the amount of air detected is greater than a predetermined amount. For example, in some embodiments the method comprises mitigating the amount of air entrained when the mass of air detected is greater than about 4%, about 4.5%, about 5%, about 5.2%, about 5.5%, about 6%, about 6.3%, about 7%, about 8%, about 8.7%, about 9%, about 10%, about 10.7%, about 11%, about 15%, about 20%, about 25%, or about 30% by mass of the fluid or fluid-entrained air composition.

In some embodiments, a method for preventing or minimizing damage to a metalworking tool includes detecting a baseline pressure of a metalworking fluid; monitoring the change in the pressure of the metalworking fluid over time; and mitigating an amount of air entrained within the metalworking fluid when the pressure of the fluid has decreased by at least about 4% or more, about 4.5% or more, about 5% or more, about 5.2% or more, about 5.5% or more, about 6% or more, about 6.3% or more, about 7% or more, about 8% or more, about 8.7% or more, about 9% or more, about 10% or more, about 10.7% or more, about 11% or more, about 15% or more, about 20% or more, about 25% or more, or about 30% or more.

In some embodiments, methods of the invention include a step of mitigating the amount of air entrained in the fluid. Mitigating may include reducing the amount of air entrained within the metalworking fluid to less than about 10%, about 7.5%, about 5.2%, about 5%, about 4%, about 3%, about 2%, about 1%, about 0.5%, about 0.1%, or about 0.05% by mass of the fluid or fluid-entrained air composition. In some embodiments, mitigating may include reducing the amount of air entrained within the metalworking fluid to about the baseline amount of air entrained within the metalworking fluid or less.

In some embodiments, mitigating the amount of air entrained in the fluid may comprise adding an additive to the metalworking fluid, preferably a defoamer. Suitable defoamers may comprise one or more of a polyacrylate, a siloxane, a silicone, and an oil. Example defoamers include one or more of a polyacrylate, a siloxane, a silicone, and an oil.

In some embodiments, a method prevents or minimizes damage to a metalworking tool. Such damage may include, but is not limited to, metal adhering to the metalworking tool, changes in surface finish, induced stress into the metal, burning of the metal part surface, dimensional changes, increased electrical energy due to loss of lubricity, changes in the type of metal chip produced, and increased breakdown of the fluid due to stresses.

EXAMPLES

Example 1. Effects of Entrained Air on Fluid Performance in the Machining of Aluminum 356-T6

Experimental

The detrimental impact of entrained air on fluid machining performance was demonstrated in both drilling and reaming of AI Alloy 356-T6. Using a metalworking fluid, Quakercool 7450-XD, which in previous testing was seen to be susceptible to rapid air entrainment, aluminum machining tests were conducted using this fluid prior to high shear mixing (minimal or low entrained air present in the fluid) and after considerable high shear mixing (high entrained air levels).

Testing was done on a Bridgeport V2XT mill using a machining test which consists of initial drilling of 110 holes in succession, followed by reaming of the drilled holes using three separate reaming speed and feed conditions. The fluid, (QC 7450-XD before and after aeration), were tested at 7% concentration in deionized water. Prior to testing and throughout the machining operations, the fluid was diverted from the supply line into the cabinet for measurement of entrained air levels (via fluid pressure measurement). Fluid performance in machining was assessed via cutting forces and BUE formation in the drilling operation, and by measurement of reamed hole finish as well as BUE formation in the reaming operation. The machining conditions used are set forth in Table 1.

TABLE 1

| Al Machining Test Method ALE (2) Machining Conditions | | | | | | | | |
|---|---|---|---|---|---|---|---|---|
| | Drilling | | Reaming | | | | | |
| | 6.35 mm | | 6.75 mm dia. Six straight flute carbide (0.255 in dia.) | | | | | |
| Tool | dia. 118° Carbide | 25 inch dia. | Reaming Condition 1 | | Reaming Condition 2 | | Reaming Condition 3 | |
| Speed | 3820 RPM | | 1500 RPM | | 2300 RPM | | 2732 RPM | |
| | 76.2 m/min | 250 SFM | 31.7 m/min | 104 SFM | 48.76 m/min | 160 SFM | 57.9 m/min | 190 SFM |
| Feed | 535.9 mm/rev | .0055 ipr | 180 mm/min | 7.1 IPM | 381 mm/min | 15 IPM | 609.6 mm/min | 24.0 IPM |
| | 0.14 mm/rev | | .119 mm/rev. | .0047 ipr | 165 1 mm/rev. | 0065 ipr | .228 mm/rev. | 0..9 ipr |
| Depth of cut | 25 mm through hole | | 25 mm through hole | | 25 mm through hole | | 25 mm through hole | |
| Coolant | External Application | | External application | | External Application | | External Application | |
| Number of Holes | 110 | | 33 Holes | | 33 Holes | | 33 Holes | |

Results

Aluminum Drilling

The level of entrained air measured during aluminum drilling experiments is presented in Table 2.

TABLE 2

| Entrained Air Measurements for Aluminum Drilling Experiments | | |
|---|---|---|
| Measurement no. | Pressure (psig) | Entrained Air (% mass) |
| Test 1 - No entrained air | | |
| 1 | 0.877 | — |
| 2 | 0.874 | — |
| 3 | 0.879 | — |
| 4 | 0.881 | — |
| 5 | 0.883 | — |
| 6 | 0.882 | — |
| Average | 0.879 | — |
| Test 2 - Entrained air | | |
| 1 | 0.807 | 8.2% |
| 2 | 0.792 | 9.9% |
| 3 | 0.785 | 10.7% |
| 4 | 0.824 | 6.3% |
| 5 | 0.801 | 8.9% |
| 6 | 0.814 | 7.4% |

Figure 7:
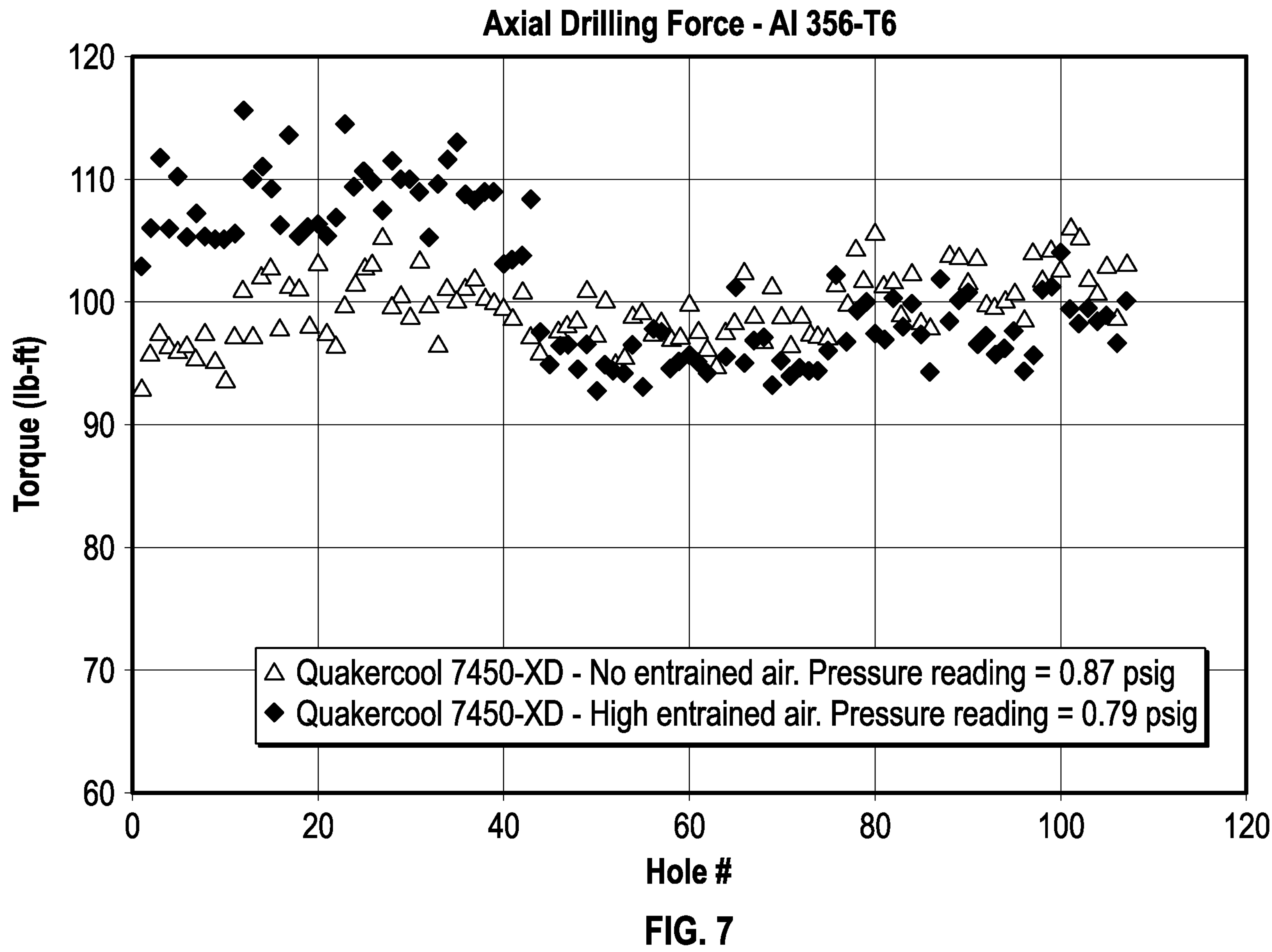
FIG. 7 illustrates the change in force of a fluid as a function of the number of holes drilled of a machining fluid with minimal entrained air and the same machining fluid with entrained air.
Figure 8:
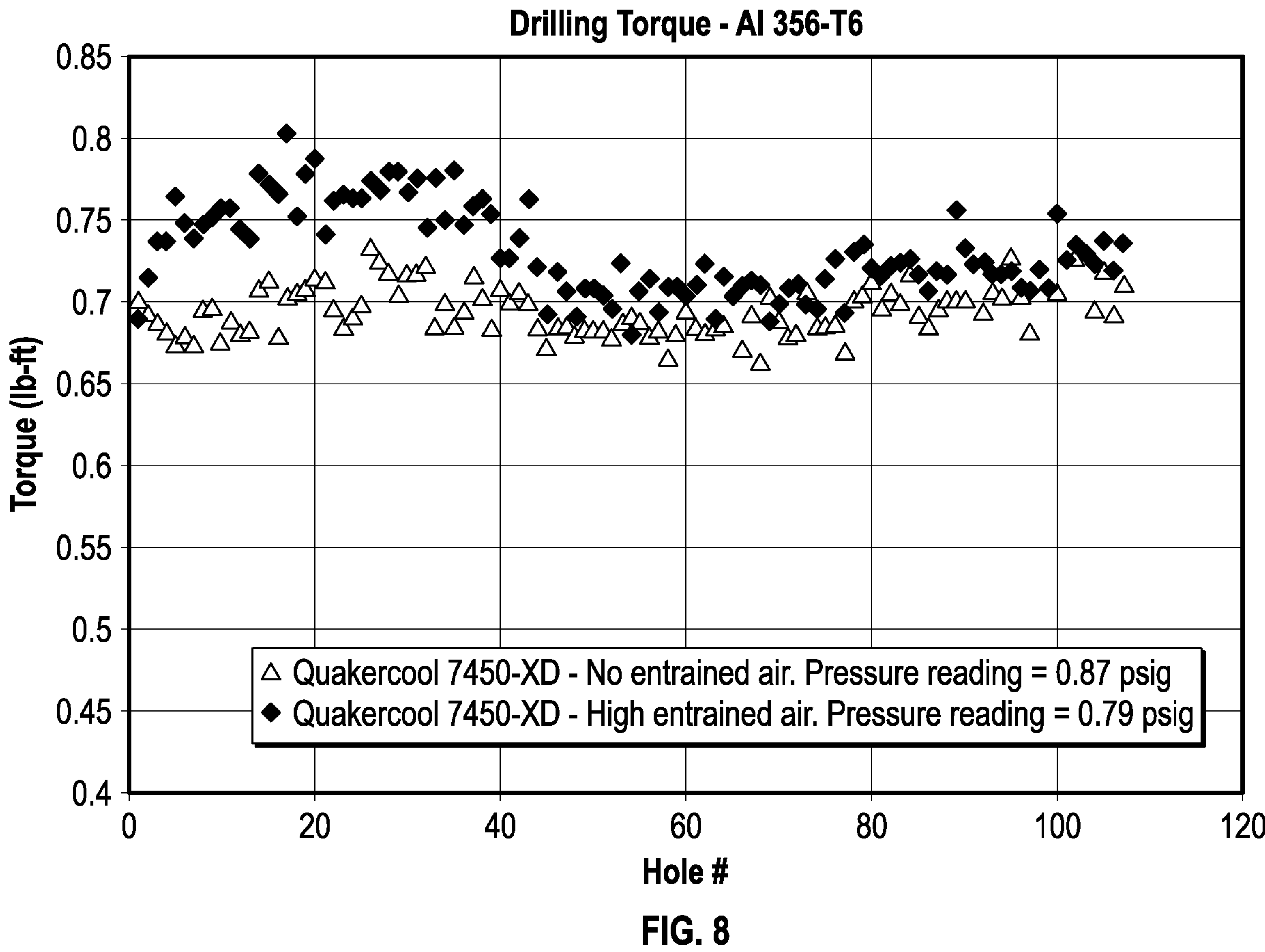
FIG. 8 illustrates the change in torque of a fluid as a function of the number of holes drilled of a machining fluid with minimal entrained air and the same machining fluid with entrained air.

During drilling, the axial forces and torque provide useful indications of a fluid's ability to provide lubrication and reduce friction during the operation, and to minimize tool wear and maintain optimum tool condition. The axial machining forces and torque obtained with the two fluids during the drilling of A1 356-T6 are shown in FIGS. 7 and 8. As seen, the fluid containing the high level of entrained air machined with higher axial cutting forces and torque over the first forty-four holes, after which point the forces lowered down to a level comparable to those measured for the control (no shear/no entrained air emulsion). The higher forces in the initial phases of the operation can be attributed to the high entrained air levels in the fluid reducing the lubrication properties of the fluid. Without being bound by theory, the reduction in forces after hole forty-four may be a result of metal adhesion (BUE) on the cutting edge altering the rake face geometry, and/or high heat formation, yielding hotter tool and resultant reduction in cutting forces. Both of these changes, while yielding reduced forces, would be expected to be very detrimental to tool performance over a longer duration of machining.

Figure 9B:
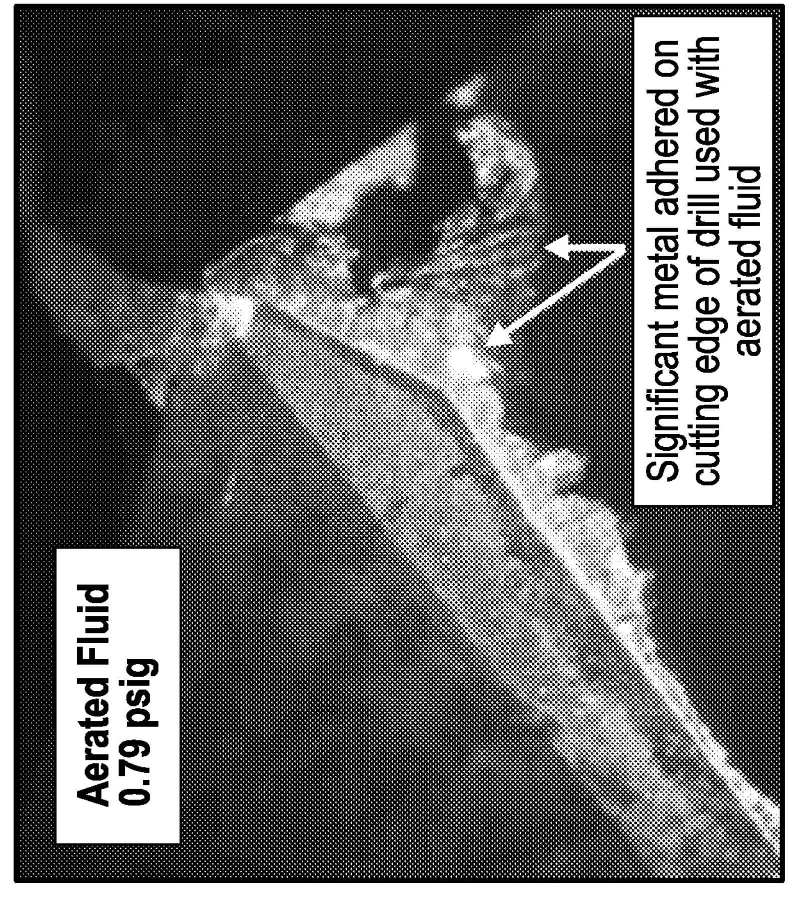
FIG. 9B illustrates the drilling tools used with a fluid with entrained air.
Figure 9A:
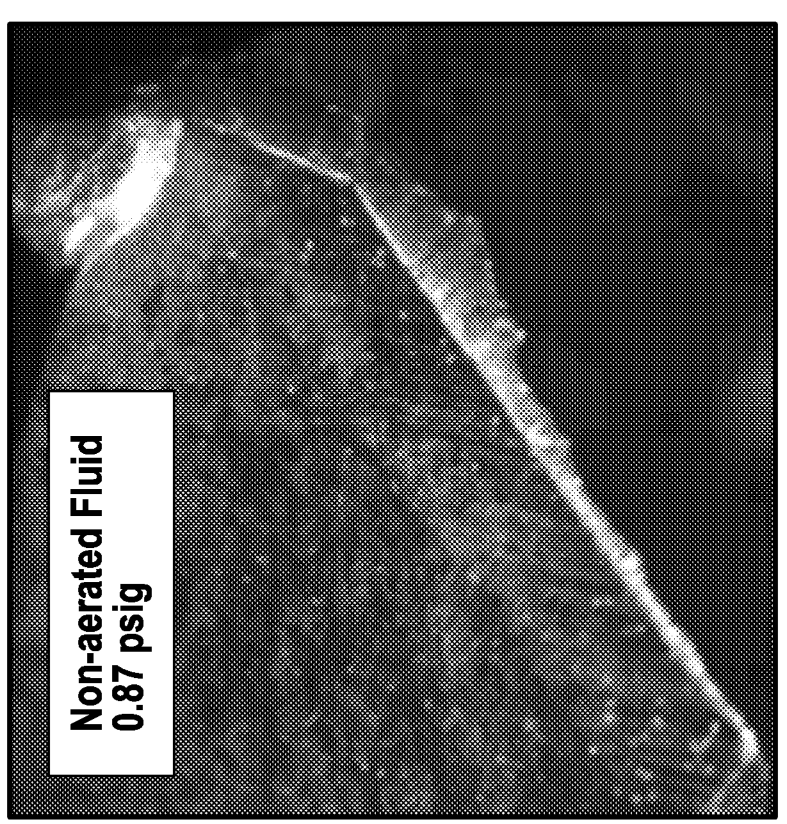
FIG. 9A illustrates the drilling tools used with a fluid with minimal entrained air.

One of the most important performance requirements of a fluid in an aluminum drilling operation is to prevent or minimize metal adhesion or built up edge formation on the cutting tool. The formation of a built up edge on the tool can lead to accelerated wear of the tool, as well as loss of hole dimensional accuracy and cylindricity. It was seen in the testing conducted that the introduction of entrained air into the fluid had a significant detrimental effect on the level of metal transfer or BUE formed on the tool's cutting edge. FIG. 9A shows images of the tools used with both the un-sheared (control) and FIG. 9B shows images of the tools used with sheared fluid (containing entrained air). The noticeably higher level of metal transfer which occurs during drilling with the air entrained fluid is clearly seen.

A quantitative measure of the level of metal adhesion formed on the drills was obtained by measuring the total area of adhered metal on the tool using a Nikon optical microscope and digital imaging software. FIGS. 10A-10D and Table 3 show the results of this analysis. As seen, air entrainment in the fluid resulted in a 58% increase in the amount of metal adhered on the tool's cutting edge.

TABLE 3

| Metal Adhesion (BUE) on Drill Edge | | | | |
|---|---|---|---|---|
| | Fluid Pressure | Edge 1 | Edge 2 | Average |
| Non-Aerated Fluid | 0.87 psig | 0.59 $mm^2$ | 0.62 $mm^2$ | 0.605 $mm^2$ |
| Aerated Fluid | 0.79 psig | 1.10 $mm^2$ | 0.81 mm2 | 0.955 $mm^2$ |

Aluminum Reaming

Figure 11:
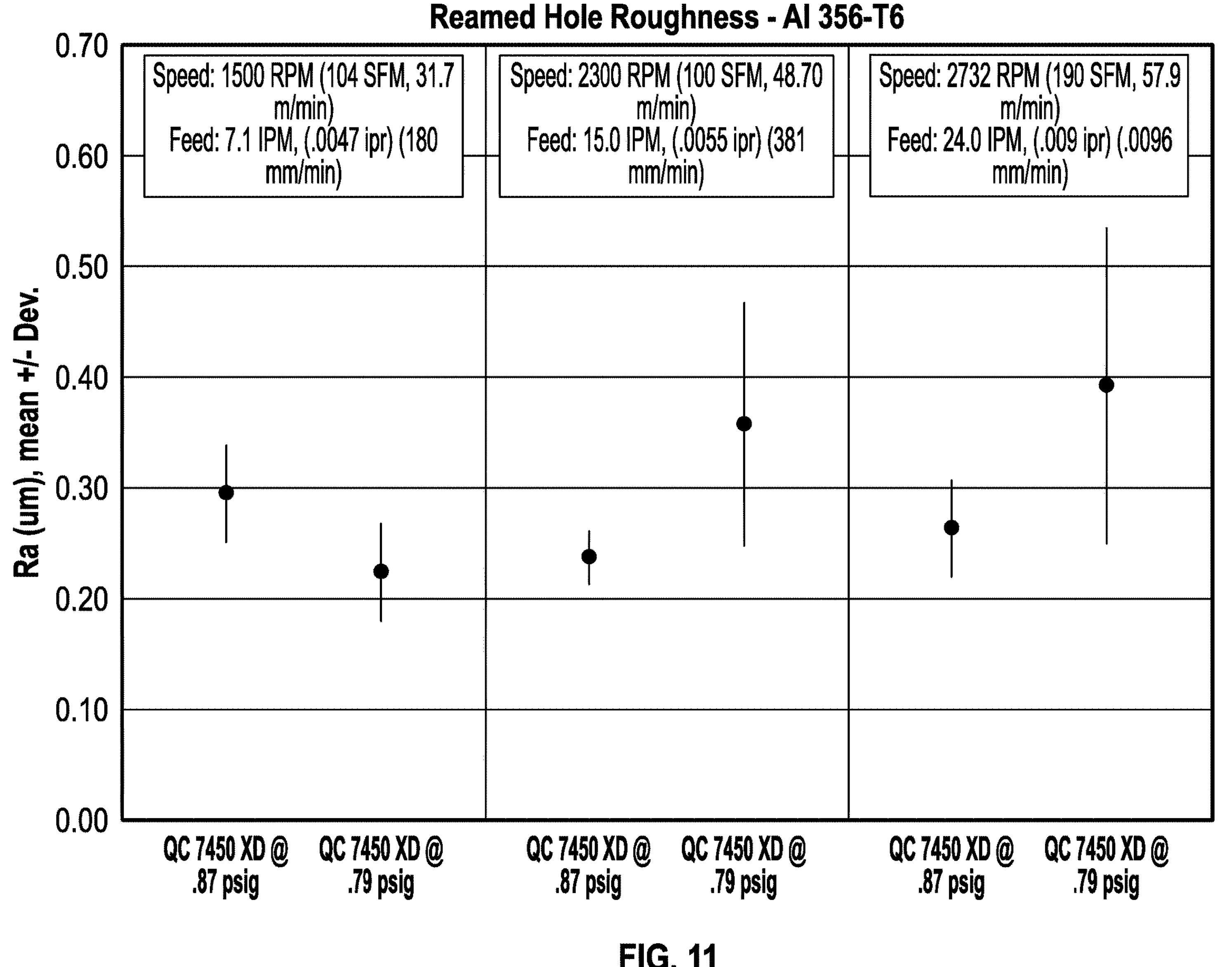
FIG. 11 illustrates the reamed hole roughness obtained using a fluid with minimal entrained air and using a fluid with entrained air for each of three reaming conditions.

Following drilling, reaming was performed at three different speeds and feeds to assess fluid performance over a range of machining conditions. The reamed hole finish obtained for the two fluids at the three reaming conditions are shown in FIG. 11. As seen, the entrainment of air in the fluid did not show a significant effect on hole roughness at the low speed and feed condition. However, at the mid and high speed/feed conditions, where consistent coolant delivery and heat removal by the fluid become increasingly important, the reamed hole roughness and consistency of the finish deteriorated significantly with the use of the aerated fluid.

The level of entrained air measured during aluminum reaming experiments is presented in Table 4.

TABLE 4

| Entrained Air Measurements for Aluminum Reaming Experiments | | |
|---|---|---|
| Measurement no. | Pressure (psig) | Entrained Air (% mass) |
| Test 1 - No entrained air | | |
| 1 | 0.883 | — |
| 2 | 0.883 | — |
| 3 | 0.884 | — |
| 4 | 0.882 | — |
| 5 | 0.882 | — |
| 6 | 0.884 | — |
| Average | 0.883 | — |
| Test 2 - Entrained air | | |
| 1 | 0.773 | 12.5% |
| 2 | 0.806 | 8.7% |
| 3 | 0.768 | 13.0% |
| 4 | 0.749 | 15.2% |
| 5 | 0.733 | 17.0% |

TABLE 4-continued

| Entrained Air Measurements for Aluminum Reaming Experiments | | |
|---|---|---|
| Measurement no. | Pressure (psig) | Entrained Air (% mass) |
| 6 | 0.732 | 17.1% |
| 7 | 0.731 | 17.2% |

Figure 12A:
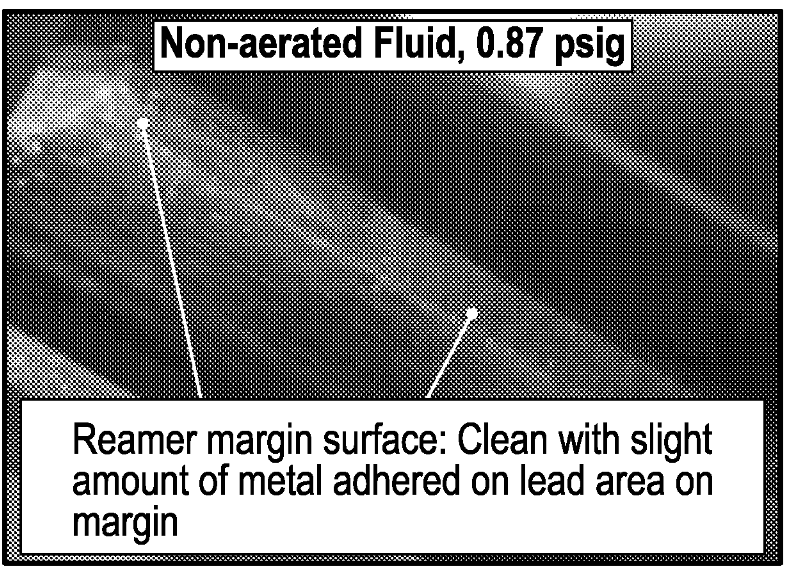
FIG. 12A and FIG. 12B illustrate a reamer surface after use with a fluid with minimal entrained air or a fluid with entrained air.
Figure 12B:
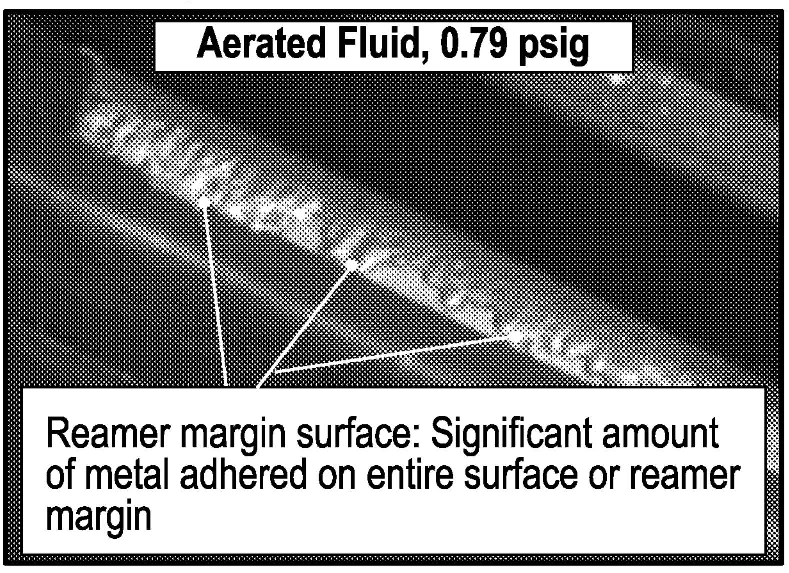

Following completion of reaming, the condition of the tools were examined under magnification. While minimal wear and BUE was observed on either reamer, it was seen that the reamer used with the entrained air containing fluid had significant deposition of a thick grease coated on the relief margin surface (shown in FIGS. 12A and 12B). This is likely a result of increased entrained air increasing friction levels, resulting in higher heat generation and/or poorer heat removal during cutting, resulting in the formation of organo-metallic greases and possibly products of oxidation depositing and adhering to the reamer surface.

Conclusions and Observations

Coolant Appearance—Introduction of entrained air had a significant effect on the appearance of the fluid during machining. The fluid became opaque white and visually foamy.

Coolant Flow and Delivery—Introduction of entrained air resulted in a severely reduced and inconsistent delivery of coolant through the system and the nozzles. This clearly imparts a significant detrimental impact on the resultant machinability in the operations performed.

Aluminum Machinability—In general, introduction of entrained air had a detrimental impact on fluid performance in the aluminum machining operations performed. Table 5 summarizes the machinability/fluid performance parameters measured and the conclusions relative to the impact of entrained air.

TABLE 5

| Fluid Performance in Aluminum Machining Operations | |
|---|---|
| Aluminum 356-T6 Drilling | |
| Axial Drilling Forces | Significant impact from entrained air with elevated forces from start of drilling to well into the operation |
| Drilling Torque | Significant impact from entrained air with elevated forces from start of drilling to well into the operation. |
| Metal Adhesion-Built-up edge | Entrained air had a large effect resulting in a significant increase in the level of workpiece metal adhered to the drill's cutting edge. Such transfer and welding of the workpiece onto the tool, can give rise to accelerated tool wear and failure, as well as loss of hole dimensional accuracy and cylindricity. |
| Aluminum 356-T6 Reaming | |
| Reamed hole roughness | Clear effect from entrained air. Especially with increasing reaming speeds and feed rates, where the aerated fluid yielded increasingly rough reamed hole finish. |
| Deposition and tool cleanliness | Entrained air in the fluid resulted in the formation and deposition of significant grease and sludge on the reamer's margin relief surface. This is likely a result of increased entrained air increasing friction levels, resulting in higher heat generation and/or poorer heat removal during cutting, resulting in the formation of organo-metallic greases and possibly products of oxidation, deposited and adhered to the reamer surface. |

Example 2. Effects of Entrained Air on Fluid Performance in the Abrasive Machining (Honing/Grinding) of Class 40 Gray Cast Iron The detrimental impact of entrained air on fluid machining performance was demonstrated in an abrasive machining operation conducted using conditions consistent with those utilized in both honing and grinding operations. The performance of a metalworking fluid, Quakercool 8013 ("QC 8013"), which in previous testing was seen to provide effective honing performance with regard to cutting efficiency and stone cleanliness, was assessed prior to high shear mixing (low or minimal entrained air present in the fluid) and after high shear mixing (high entrained air levels in the fluid).

Figure 13A:
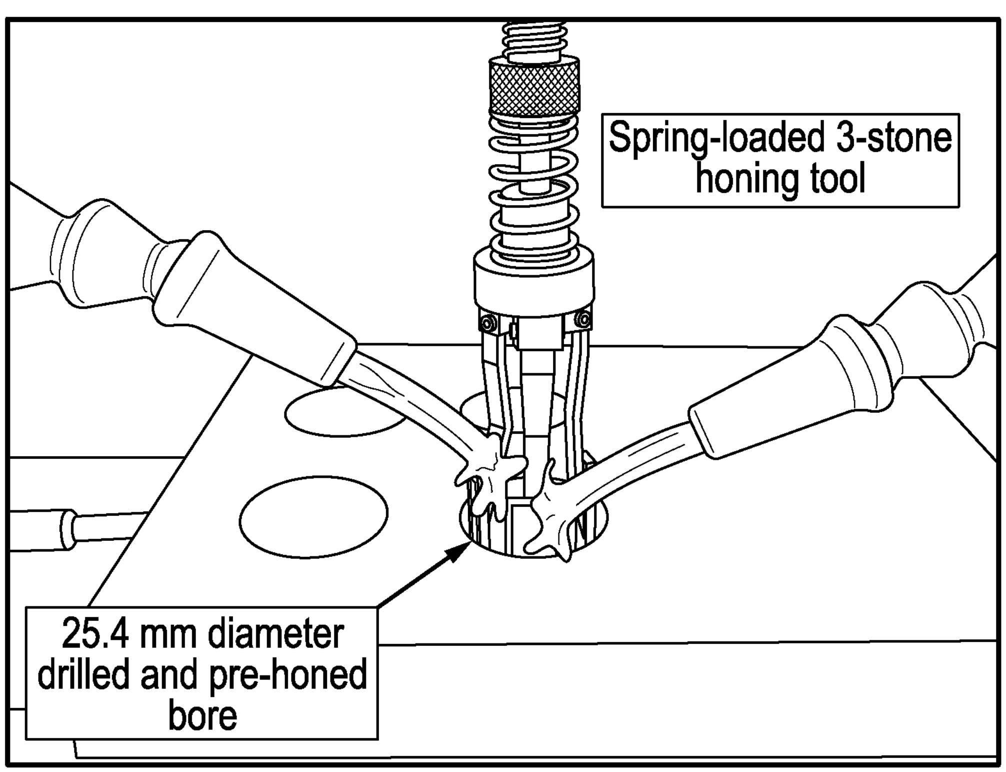
FIG. 13A, FIG. 13B, and FIG. 13C illustrate honing stones used with a fluid with minimal entrained air or a fluid with entrained air.
Figure 13B:
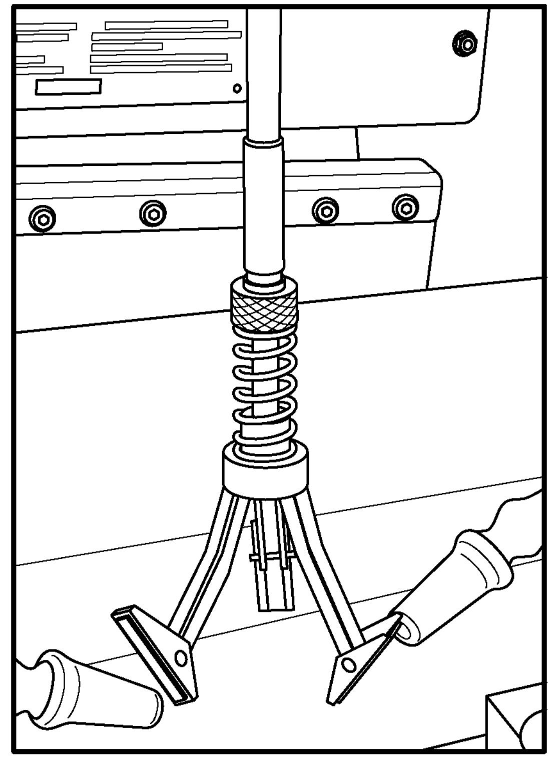
Figure 13C:
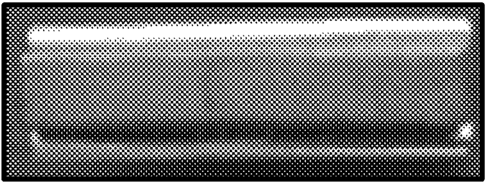
Figure 14A:
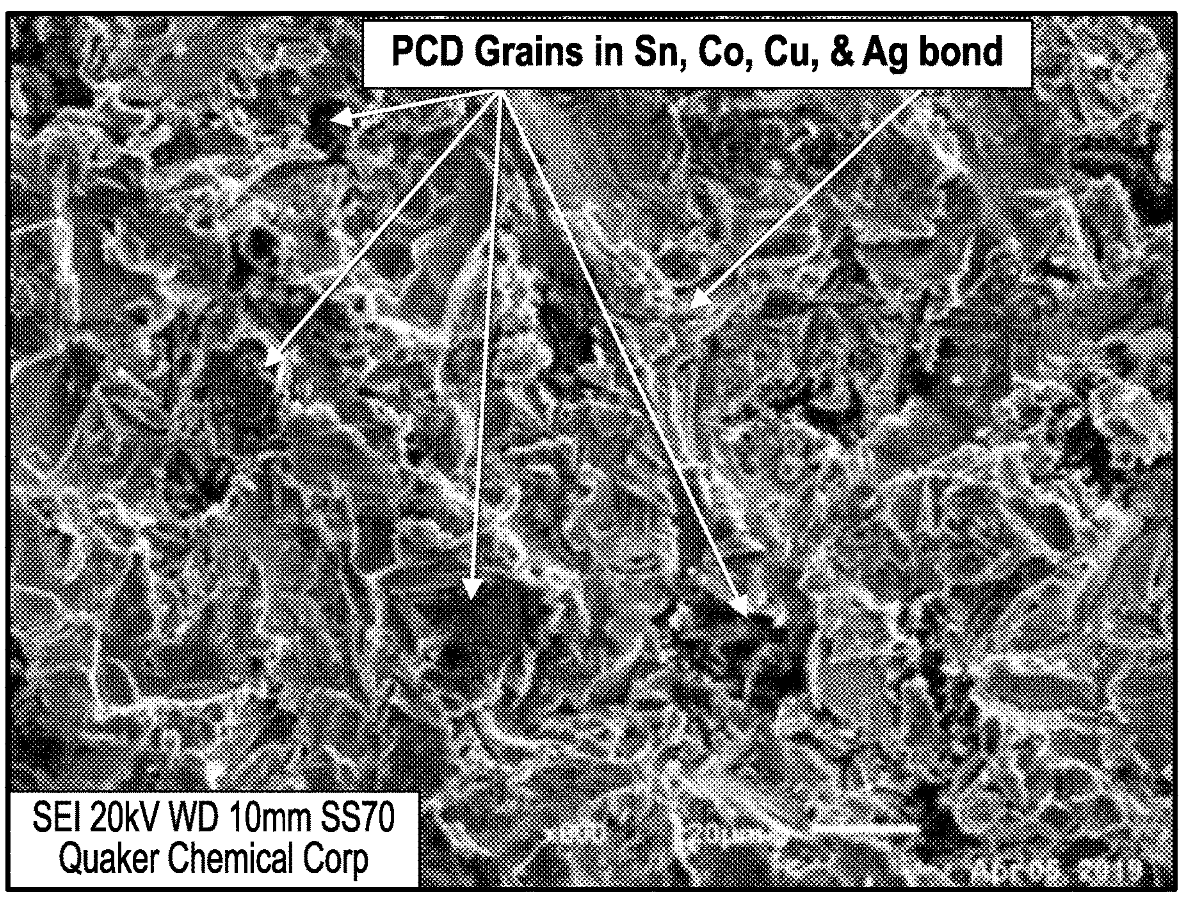
FIGS. 14A, FIG. 14B, FIG. 14C, FIG. 14D, FIG. 14E, FIGS. 14F, and 14G illustrate scanning electron microscope (SEM) images of the stone surfaces of a stone used with the stone honing tool shown in FIGS. 13A-13C.
Figure 14B:
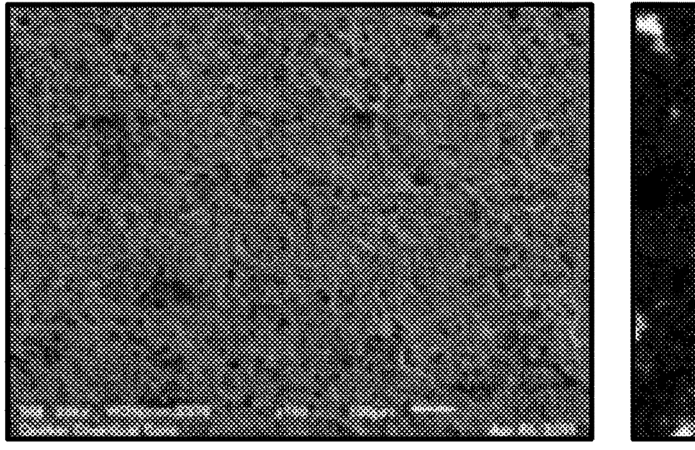
Figure 14C:
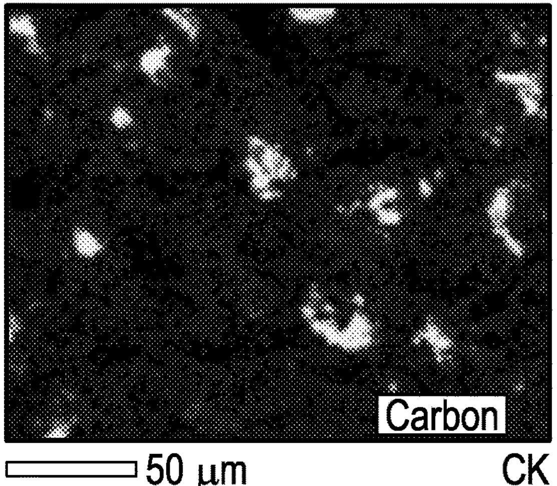
Figures 14D, 14E, 14F, 14G:
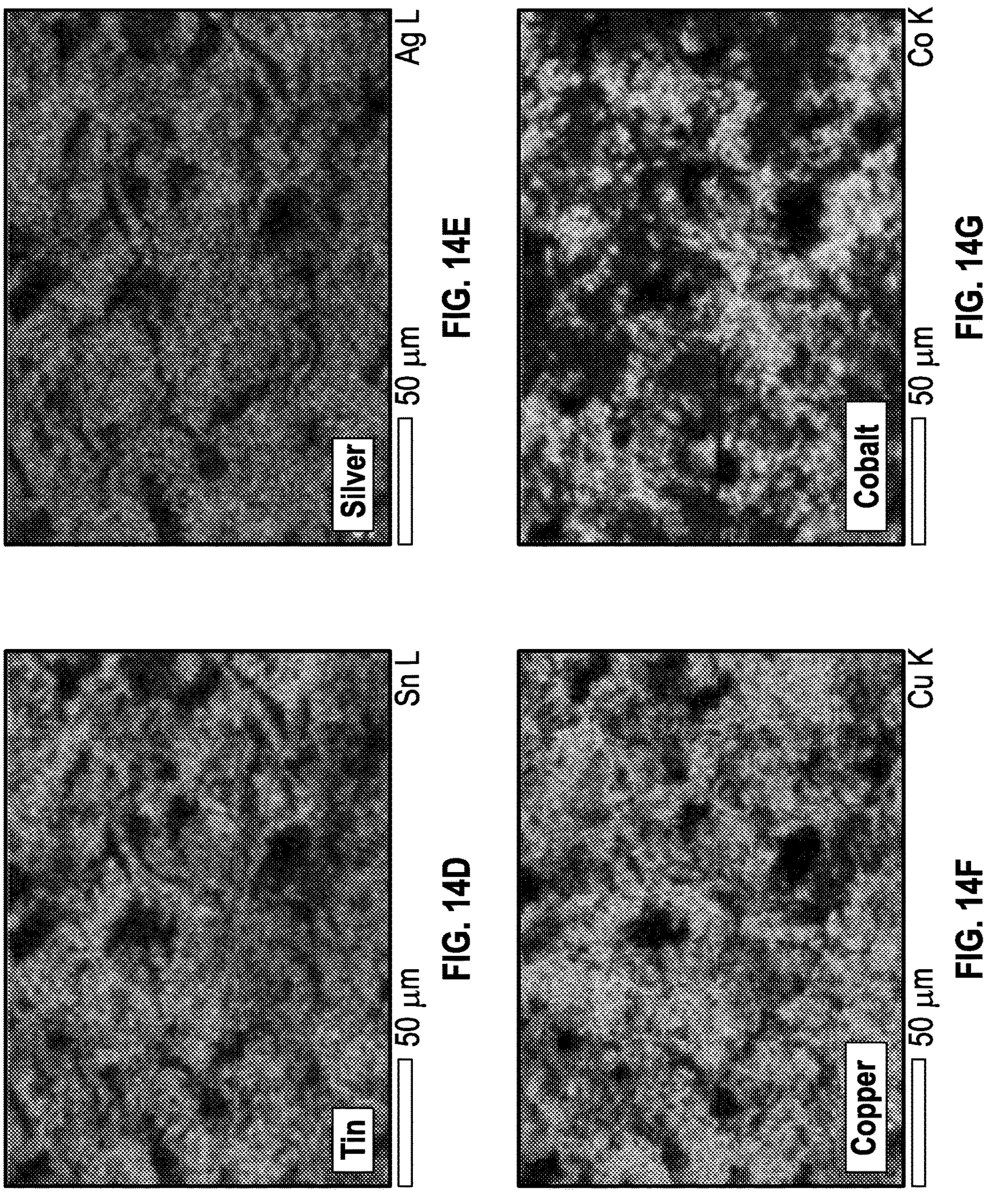
Figure 15:
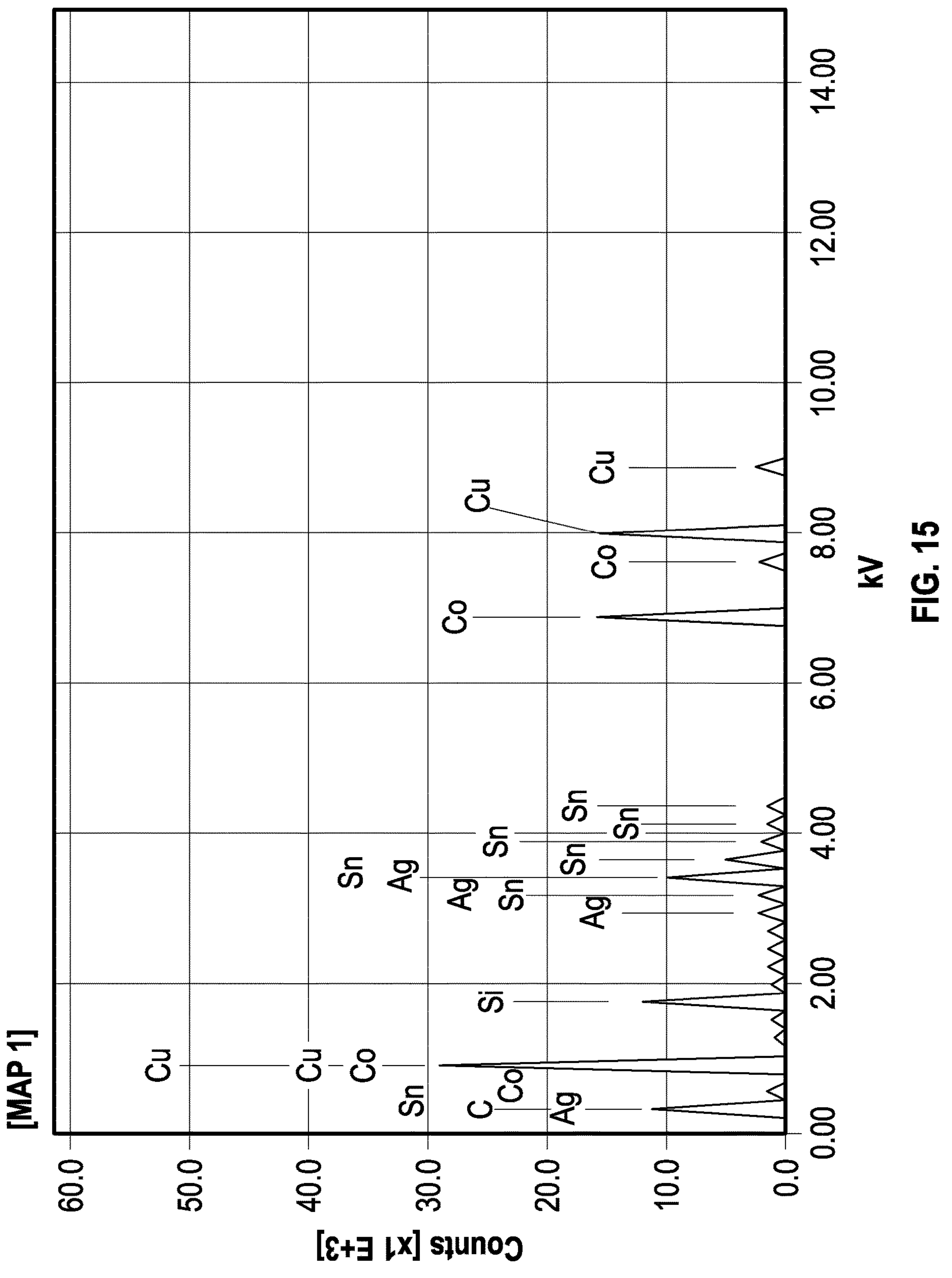
FIG. 15 provides an energy dispersive x-ray (EDX) spectroscopic analysis of the stone imaged in FIGS. 14A-14G.

Using a vertical machine tool (Bridgeport V2XT), tests were conducted using a three stone honing tool with a constant expansion pressure of 0.057 MPa. Honing is performed on the interior surface of a 25.4 mm diameter Class 40 gray cast iron bore pre-drilled and reamed to an initial surface roughness of 2.2-3.0 μm Ra. Images of the workpiece and the honing tool are shown in FIGS. 13A-13C. The constant expansion force is provided by a compressed spring in the loading system of the honing tool which can be adjusted to the desired force. Each honing tool contains three 28 mm×5 mm×3 mm honing stones comprised of 600 grit diamond abrasive grains in a tin/silver/copper/cobalt matrix. Scanning electron microscopic images are shown in FIGS. 14A-G and results of energy dispersive x-ray spectroscopic analysis of the stone surface are shown in FIG. 15.

Figure 16:
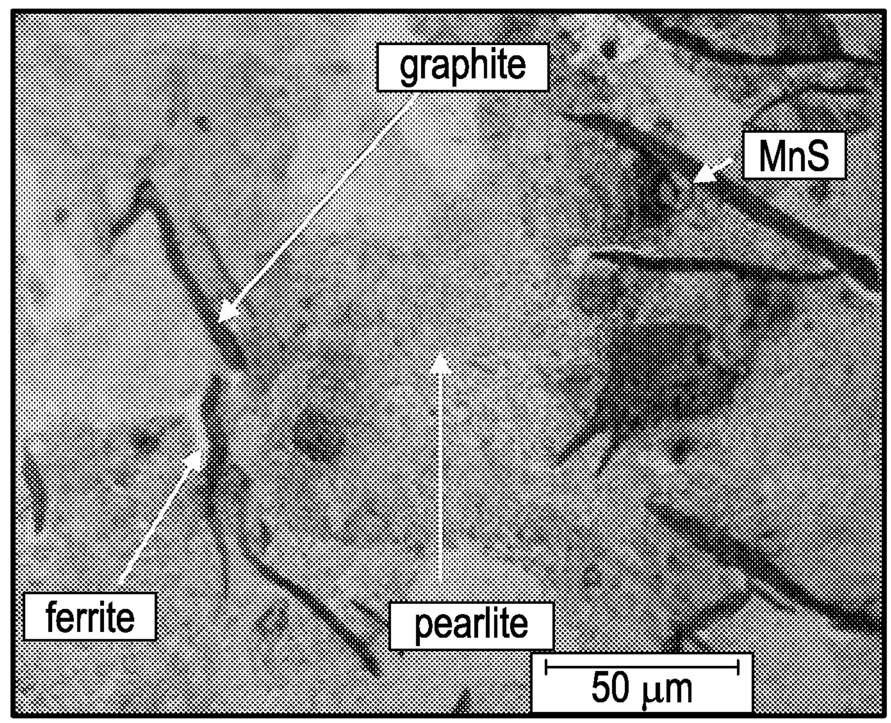
FIG. 16 provides an optical micrograph (500×) of an etched metal specimen.

The workpiece used is a Class 40 pearlitic gray iron containing Type A graphite, consistent with specifications within ASTM A48 Class 40. The microstructure of this workpiece is shown in FIG. 16. Along with the graphite and regions of pearlite, the presence of manganese sulfide is also seen. To prepare this material for the honing test, 25.4 mm diameter through-holes were drilled and subsequently reamed in a 101.6 mm×101.6 mm×38.1 mm test block, to yield a starting bore surface roughness of 2.2-3.0 μm Ra.

The honing test was conducted at 400 RPM (36 m/min) at a feed rate of 3.175 mm/rev. Each test consisted of running 1500 cycles, with each cycle consisting of the tool feeding down to the bottom of the bore and then retracting back up to the top of the bore. Measurement of honing performance parameters were made at the beginning of the test, and then at certain cycle intervals during the test. The performance parameters measured consist of cutting efficiency (level of metal cut) and metal adhesion, i.e., loading on the stone surface. Using a Vernier caliper, metal removal rate was obtained by measuring the increase in workpiece diameter which occurs as honing continues. Assessment of the degree of metal adhesion and loading on the stone surface was made via optical microscopy. Each fluid (QC 8013 w/o entrained air and QC 8013 with entrained air) was tested at 7% concentration in deionized water, and coolant delivery was done via an external flood application. Details of the honing conditions are shown in Table 6.

TABLE 6

| Honing Conditions | |
|---|---|
| Stone | 600 grit metal bonded diamond |
| Bore Diameter (ID) | 25.4 mm |
| Spindle Speed (RPM) | 400 |
| Rotational Speed (m/min) | 36 m/min |
| Rotational Speed (m/sec) | 0.6 m/sec |
| Feed Rate | 1270 mm/min (3.175 mm/rev) |
| Expansion Pressure | 0.14 Mpa |
| Workpiece | Gray Cast Iron |

The level of entrained air measured during Class 40 Gray Cast Iron honing experiments is presented in Table 7.

TABLE 7

Entrained Air Measurements for Class 40 Gray Cast Iron Honing Experiments

| Measurement no. | Pressure (psig) | Entrained Air (% mass) |
|---|---|---|
| Test 1 - No entrained air | | |
| 1 | 0.889 | — |
| 2 | 0.883 | — |
| 3 | 0.885 | — |
| 4 | 0.886 | — |
| 5 | 0.891 | — |
| 6 | 0.901 | — |
| Average | 0.889 | — |
| Test 2 - Entrained air | | |
| 1 | 0.837 | 5.2% |
| 2 | 0.831 | 5.9% |
| 3 | 0.791 | 10.4% |

TABLE 7-continued

Entrained Air Measurements for Class 40 Gray Cast Iron Honing Experiments

| Measurement no. | Pressure (psig) | Entrained Air (% mass) |
|---|---|---|
| 4 | 0.793 | 10.2% |
| 5 | 0.784 | 11.2% |
| 6 | 0.785 | 11.1% |
| 7 | 0.778 | 11.9% |
| 8 | 0.792 | 10.3% |
| 9 | 0.804 | 8.9% |
| 10 | 0.806 | 8.7% |

Fluid Performance and Effects of Entrained Air—Metal Cutting Efficiency

Figure 17:
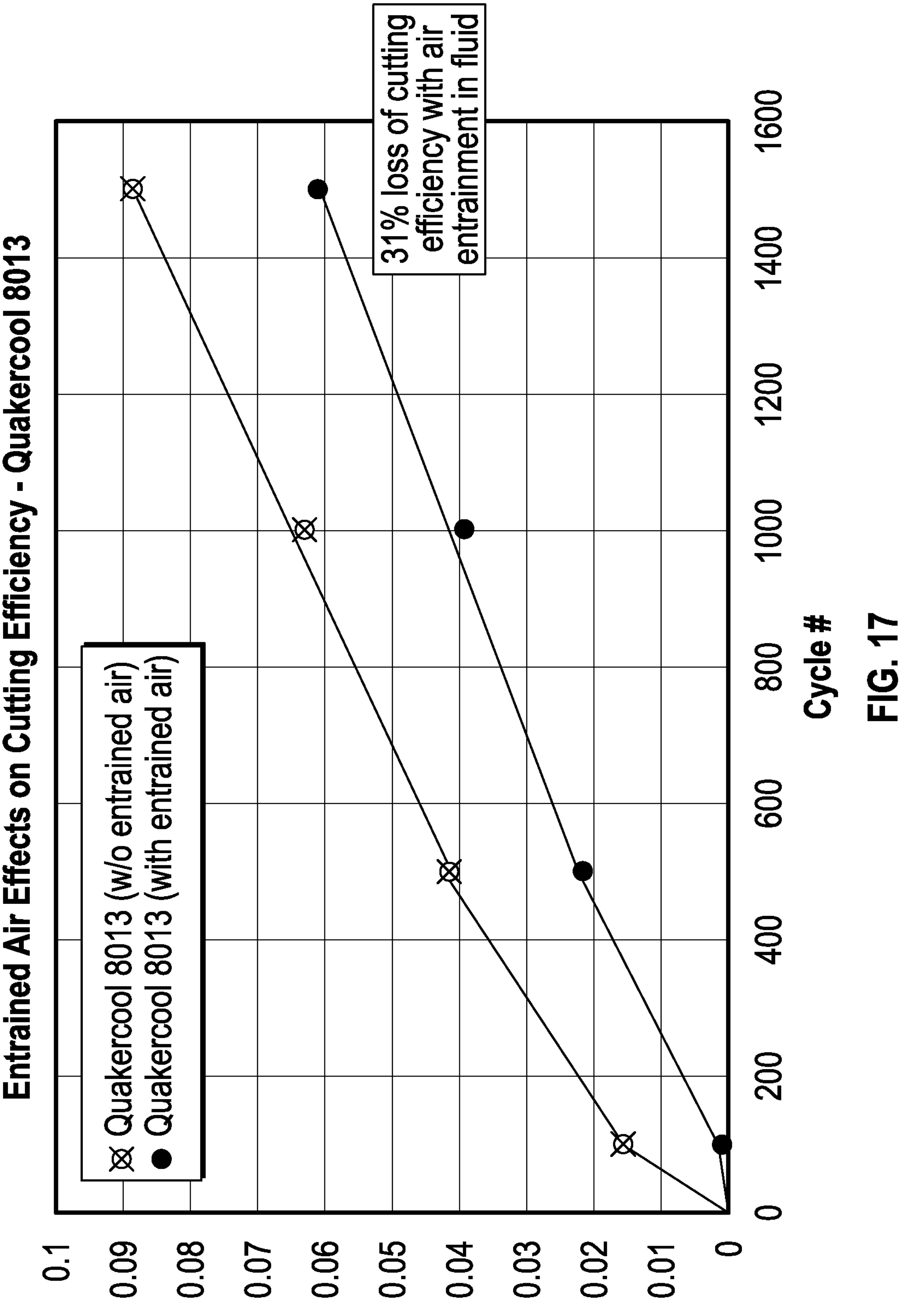
FIG. 17 provides a plot of the volume of metal cut ($in^3$) as a function of number of cycles using a Quakercool 8013 fluid with minimal entrained air and a Quakercool 8013 fluid with entrained air.

A fluid's ability to enable free cutting at an optimum cutting rate is critical for maintaining desired cycle times in a honing operation as well as achieving the desired surface roughness and texture. A low cutting efficiency can potentially arise from various factors such as abrasive wear of the stone, metal adhesion and loading on the stone surface, as well as a non-optimum level of lubrication provided by the fluid. In the honing test conducted, the cutting 10 efficiency was determined by measurement of the increase in the honed bore diameter which occurs over the 1500 honing cycles. Measurements made after 100, 500, 1000, and 1500 cycles were plotted and utilized for examining the cutting efficiency of the fluids. As seen in FIG. 17, the entrainment of air into Quakercool 8013 had a significant detrimental effect on cutting efficiency This was seen from the early stages of the process (100-500 cycles), and continued through the entire 1500 cycles, giving an overall 31% loss of cutting efficiency relative to that measured using Quakercool 8013 with no entrained air. This loss of cutting efficiency is due to a significant amount of metal and residue adhesion on the stones reaching a level which inhibits free cutting of the workpiece.

Performance and Effects of Entrained Air—Metal Adhesion/Stone Loading

Figure 18A:
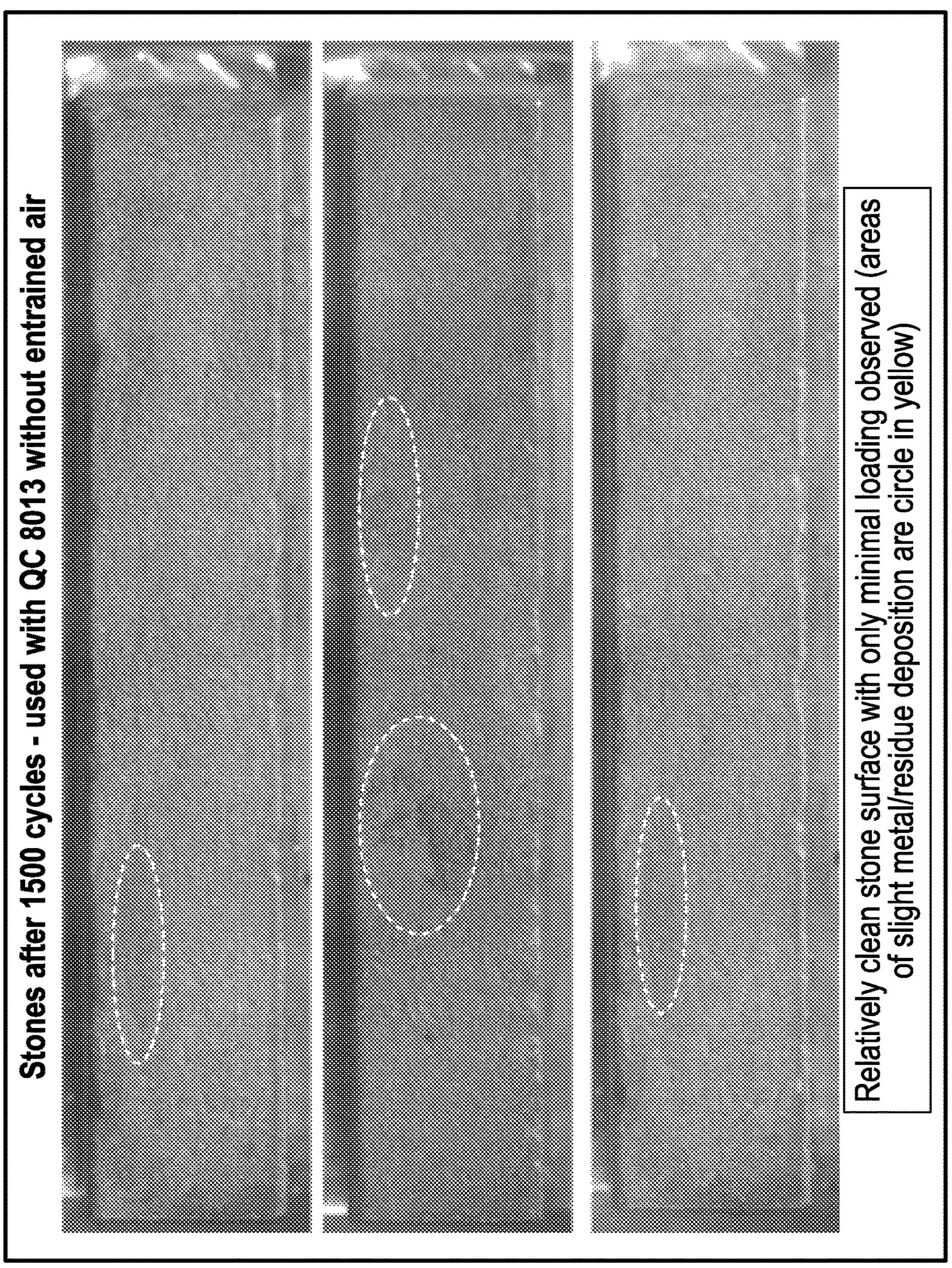
FIG. 18A and FIG. 18B provide pictures of metal and organo-metallic deposits on surfaces of a honing stone.
Figure 18B:
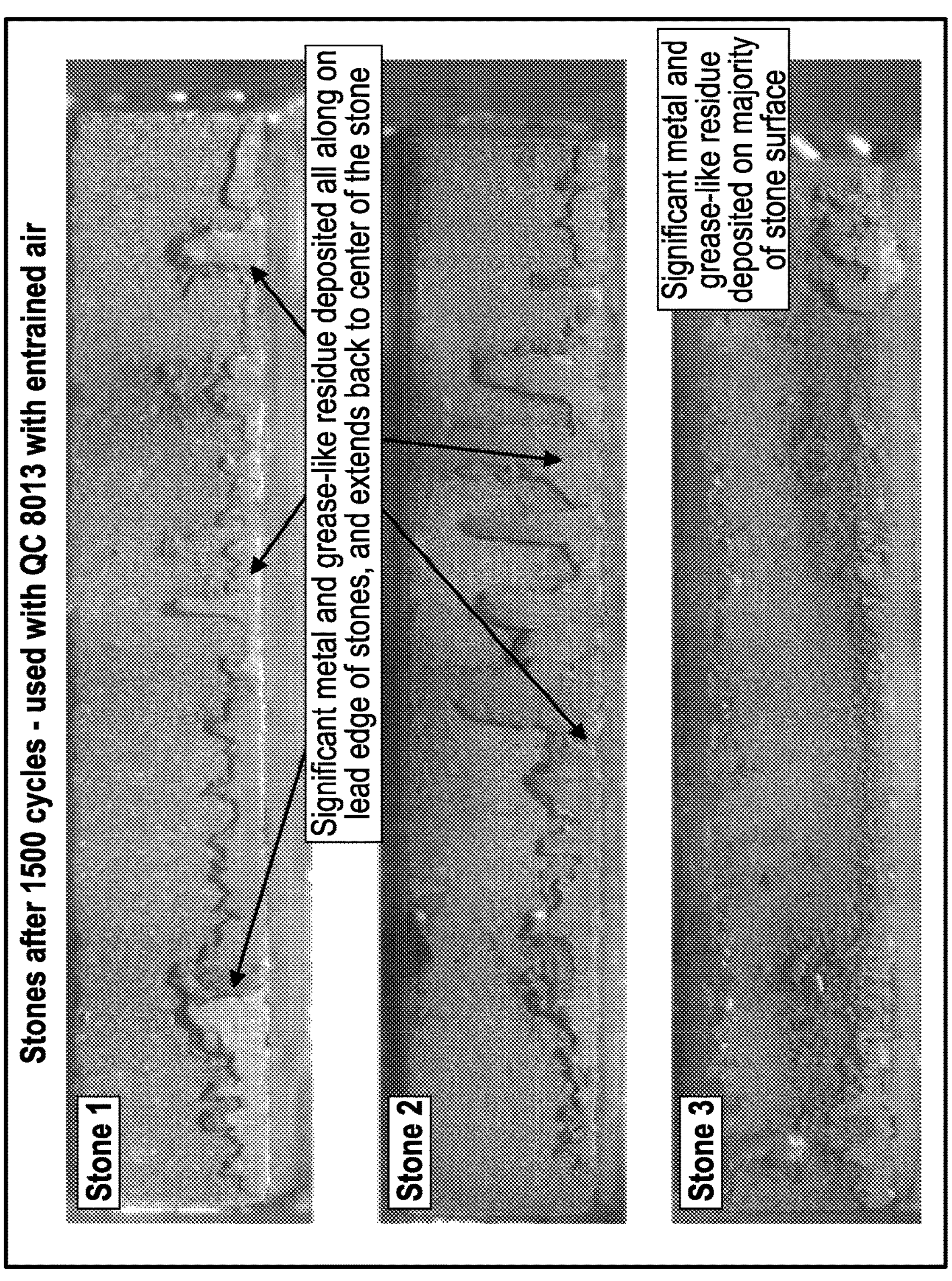

Adhesion and loading of metal and organo-metallic deposits onto the honing stone surface is probably the most critical factor impacting cutting efficiency and surface roughness during the honing process. The measure of the degree of metal adhesion and loading which has occurred on the stone surface was made by visual examination of the stone surfaces under magnification, and also by measurement of the total area of the stone surface where loading occurred. Results obtained are shown in FIGS. 18A and 18B and Table 8. As seen by both visual examination of the stone surfaces (FIGS. 18A and 18B), and by the areas of deposition as measured using a digital software measurement system (Table 8), air entrainment in the fluid resulted in a significant increase in deposition of metallics and organo-metallics onto the stone surface. As mentioned previously, such deposition and loading will have a significant detrimental effect on stone life and performance.

TABLE 8

| Measured Deposition and Loading on Stone Surface | | | | |
|---|---|---|---|---|
| | Quakercool 8013 (w/o entrained air) | | Quakercool 8013 (with entrained air) | |
| | Area of Loading ($mm^2$) | % of Stone Surface where loading occurred | Area of Loading ($mm^2$) | % of Stone Surface where loading occurred |
| Stone 1 | 0.74 | 4.31 | 4.32 | 25.19 |
| Stone 2 | 0.65 | 3.79 | 6.31 | 36.79 |
| Stone 3 | 0.75 | 4.37 | 11 | 64.14 |
| Average | 0.71 | 4.16 | 7.21 | 42.04 |

Example 3. Effects of Entrained Air on Fluid Performance in the Tapping of 1018 Steel The detrimental impact of entrained air on fluid machining performance was demonstrated in form tapping of Steel Alloy 1018. Using a metalworking fluid, Hocut 795-MPC, which in previous testing was seen to be susceptible to rapid air entrainment, steel machining tests were conducted using this fluid prior to high shear mixing (minimal or low entrained air present in the fluid) and after considerable high shear mixing (high entrained air levels).

Testing was done on a MicroTap™ Labtap™ tapping instrument using a machining test which consists of form tapping pre-drilled holes in a steel test bar. The fluid, (Hocut 795-MPC), before and after aeration were tested at 5% concentration in deionized water. Prior to testing and throughout the machining operations, the fluid was diverted from the supply line into the cabinet for measurement of entrained air levels (via fluid pressure measurement). Fluid performance was assessed via tapping torque values. The machining conditions used are set forth in Table 9.

TABLE 9

| Machining Conditions | |
|---|---|
| | Tapping |
| Tool | M6 × 1.0 form tap |
| Speed | 600 RPM |
| Depth of form | 3/8 in |
| Hole diameter | 5.55 mm |
| Test metal | Steel 1018 |
| Numbers of holes | 22 |

Results

Steel Tapping

Figure 19:
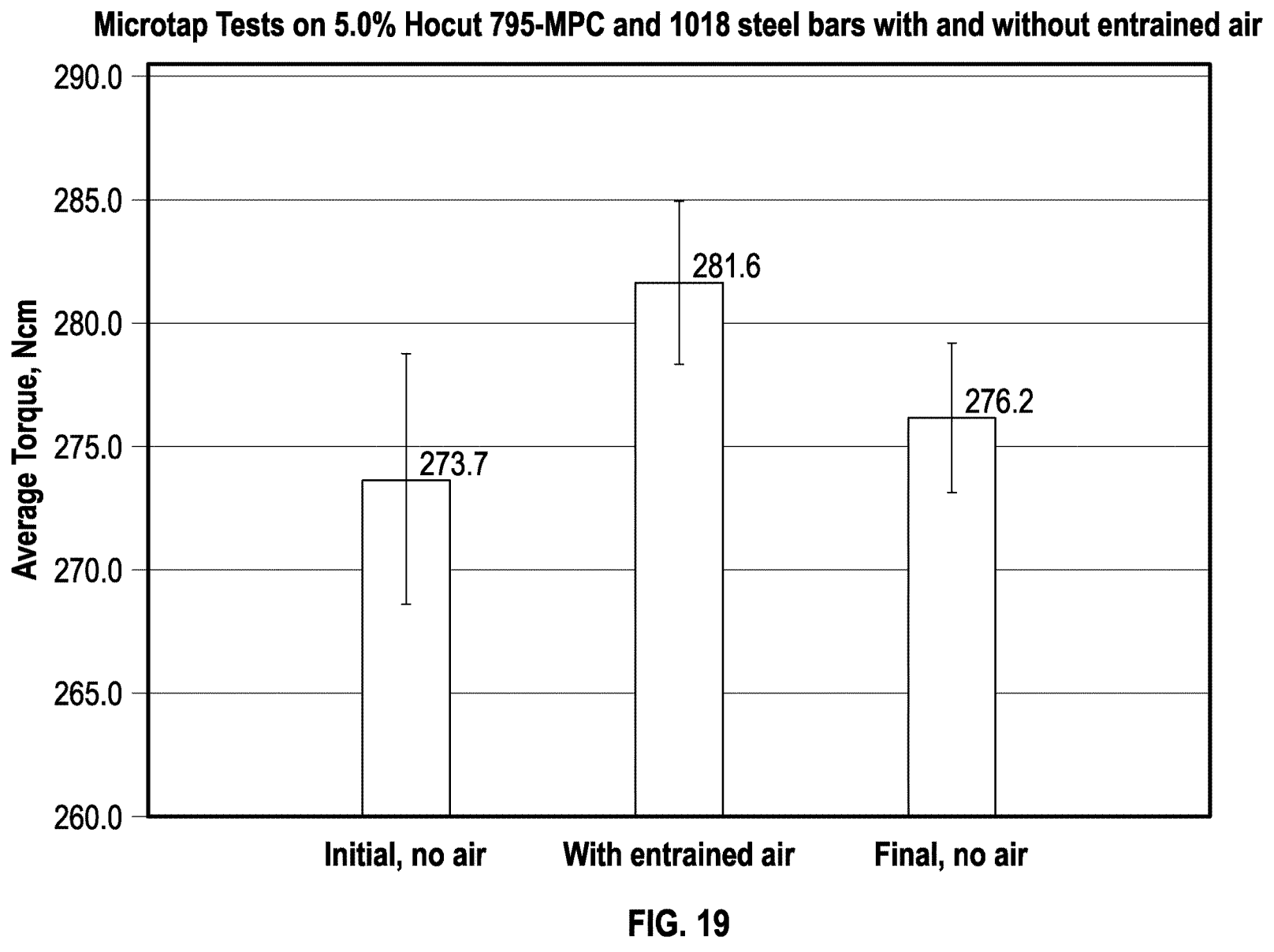

During tapping, the torque measurements provide useful indications of a fluid's ability to provide lubrication and reduce friction during the operation, and to minimize tool wear and maintain optimum tool condition. The torque measurements obtained with the two fluids during the tapping of Steel 1018 are shown in FIG. 19. The tests were as follows: (1) test with no entrained air, (2) test with entrained air, and then another test (3) where the air was allowed to release from the fluid. As seen, the fluid containing the high level of entrained air machined with higher torque levels compared to the fluid containing no entrained air. The level of entrained air measured in each test is provided in Table 10.

TABLE 10

| Entrained Air Measurements for Tapping Experiments | | |
|---|---|---|
| Measurement no. | Pressure (psig) | Entrained Air (% mass) |
| Test 1 - No entrained air | | |
| 1 | 0.892 | — |
| 2 | 0.893 | — |
| 3 | 0.893 | — |
| 4 | 0.894 | — |
| 5 | 0.893 | — |
| 6 | 0.895 | — |
| Average | 0.893 | — |
| Test 2 - Entrained air | | |
| 1 | 0.645 | 27.8% |
| 2 | 0.629 | 29.6% |
| 3 | 0.633 | 29.1% |
| 4 | 0.630 | 29.5% |
| 5 | 0.638 | 28.6% |
| 6 | 0.633 | 29.1% |
| 7 | 0.631 | 29.4% |
| 8 | 0.632 | 29.3% |
| Test 3 - No entrained air | | |
| 1 | 0.885 | — |
| 2 | 0.884 | — |
| 3 | 0.885 | — |
| 4 | 0.884 | — |
| 5 | 0.883 | — |
| Average | 0.884 | — |

Conclusions and Observations

The introduction of entrained air had a significant effect on the appearance of the fluid during machining; the fluid became more opaque white and visually foamy. The introduction of entrained air resulted in a severely reduced and inconsistent delivery of coolant through the system and the nozzles. This clearly imparts a significant detrimental impact on the resultant machinability in the operations performed. Additionally, in general, introduction of entrained air had a detrimental impact on fluid performance in the form of tapping of steel due to the increase in torque required to tap the holes.

The conclusions and observations for Examples 1-3 are summarized in Table 11.

TABLE 11

| Entrained Air Testing Summary | | |
|---|---|---|
| Operation | Entrained air level | Entrained air effect |
| Tapping | 27.8-29.6% | 2.9% increase in torque - direct indication in loss of lubricity |
| Drilling | 6.3-10.7% | 58% increase in metal adhered to drill |
| Reaming | 8.7-17.2% | Increased surface roughness and material on reamer |
| Honing | 5.2-11.9% | 31% loss in cutting efficiency |

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method for preventing or minimizing damage to a metalworking tool during use in a metalworking operation, the method comprising:

monitoring of an amount of air entrained within a metalworking fluid in-use with and fluidly connected to the metalworking tool during the metalworking operation;

the monitoring comprising:

passing the fluid substantially vertically through a fluid conduit;

stopping the flow of the fluid through the fluid conduit at a first time point;

measuring the pressure of the fluid at a first position along the fluid conduit at the first time point, a second time point, and a final time point to acquire a first pressure measurement, a second pressure measurement, and a final pressure measurement;

calculating the density of the fluid at the first time point, the second time point, and the final time point from the pressure of the fluid at the first time point, the second time point, and the final time point, respectively;

calculating a change in density of the fluid as a function of time; and calculating an amount of entrained air and/or foam within the fluid at the first time point based on the change in density of the fluid as a function of time; and mitigating the amount of air entrained within the metalworking fluid fluidly connected to the metalworking tool in use in the metalworking operation when the amount of air determined is 4% by mass of the metalworking fluid or greater, thereby preventing or minimizing damage of the metalworking tool during the metalworking operation.

2. The method of claim 1, wherein the metalworking tool is used within a metalworking system, the metalworking system designed to carry out a machining operation, an impact deformation process, and/or a pressure deformation process.

3. The method of claim 2, wherein:

the machining operation comprises one or more of: drilling, boring, reaming, tapping, thread rolling, thread chasing, hobbing, milling, turning, sawing, planning, scraping, shearing, shaving, broaching, cutting, polishing, and burnishing; and the impact deformation process comprises one or more of stamping, and forging; and the pressure deformation process comprising one or more of hydroforming and sintering.

4. The method of claim 2, wherein the method further comprises dispensing a foam/entrained air control agent into the metalworking system.

5. The method of claim 1, wherein the metalworking fluid is used in one or more processes comprising metal removal, metal treating, metal protecting, metal forming, and metal cleaning.

6. The method of claim 1, wherein the pressure and/or density is measured using one or more pressure transducers.

7. The method of claim 1, wherein the step of monitoring the amount of air entrained within the metalworking fluid further comprises correlating the pressure measurement with a mass of entrained air within the metalworking fluid.

8. The method of claim 1, wherein the pressure measurement at the first time point is a baseline pressure measurement taken prior to disturbance of the metalworking fluid.

9. The method of claim 1, wherein the pressure measurement at the second time point is a measurement taken subsequent to a disturbance of the metalworking fluid, and wherein a reduction in the pressure measurement at the second time point in comparison to the pressure measurement at the first time point is attributable to an increase in entrained air within the metalworking fluid.

10. The method of claim 1, wherein the metalworking tool damage prevented or minimized comprises one of more of metal adhering to the metalworking tool, changes in surface finish of the metalworking tool, induced stress into the metal of the metalworking tool, burning of a metal part surface of the metalworking tool, dimensional changes of the metalworking tool, increased electrical energy due to loss of lubricity, changes in the type of metal chip produced, and increased breakdown of the fluid due to stresses.

* * * * *